(12) United States Patent
Turner et al.

(10) Patent No.: US 7,019,126 B1
(45) Date of Patent: Mar. 28, 2006

(54) TRANSGENIC PLANTS PRODUCING A PAP II PROTEIN

(75) Inventors: Nilgun E. Turner, Belle Mead, NJ (US); Pinger Wang, Piscataway, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 342 days.

(21) Appl. No.: 09/721,047

(22) Filed: Nov. 22, 2000

Related U.S. Application Data

(63) Continuation of application No. PCT/US99/11301, filed on May 21, 1999.

(60) Provisional application No. 60/086,374, filed on May 22, 1998.

(51) Int. Cl.
| C07K 14/00 | (2006.01) |
| C12N 5/14 | (2006.01) |
| C12N 15/00 | (2006.01) |
| A01H 11/00 | (2006.01) |
| A01H 5/00 | (2006.01) |

(52) U.S. Cl. .................. 536/24.1; 536/23.1; 536/24.1; 536/350; 800/295; 800/298; 800/317.3; 435/321.1; 435/430

(58) Field of Classification Search ............... 536/23.1; 435/320.1, 419; 800/301, 317.3, 295, 279, 800/298

See application file for complete search history.

(56) References Cited

U.S. PATENT DOCUMENTS

| 5,304,730 A | 4/1994 | Lawson | 800/280 |
| 5,756,322 A | 5/1998 | Turner | 530/370 |
| 5,880,329 A | 3/1999 | Turner | 800/301 |
| 6,137,030 A | 10/2000 | Turner | 800/279 |

FOREIGN PATENT DOCUMENTS

FR  2699553 A1  6/1994

OTHER PUBLICATIONS

Poyet, et al., FEBS Letters, 347:268-272 (1994).
Lodge, et al., Proceedings of the National Academy of Sciences 90:7089-7093 (1993).
Hur, et al., Proc. Natl. Acad. Sci. USA, 92:8448-8452 (1995).
Abel, et al., Science 232:738-43 (1986).
Cuozzo, et al., Bio/Technology 6:549-57 (1988).
Hemenway, et al., EMBO J. 7:1273-80 (1988).
Stark, et al., Bio/Technology 7:1257-62 (1989).
Lawson, et al., Bio/Technology 8:127-34 (1990).
Kawchuk, et al., Mol. Plant-Microbe Interactions 3(5):301-07 (1990).
Irvin, et al., Pharmac. Ther. 55:279-302 (1992).
Endo, et al., Biophys. Res. Comm. 150:1032-36 (1988).
Hartley, et al., FEBS Lett. 290:65-68 (1991).
Beachy, et al., Ann. Rev. Phytopathol. 28:451-74 (1990).
Golemboski, et al., Proc. Natl. Acad. Sci. USA 87:6311-15 (1990).
Hayashi, et al., J. Bioenerg. Biomem. 22:451-71 (1990).
Dore, et al., Nuc. Acids Res. 21(18):4200-05 (1993).
Monzingo, et al., J. Mol. Biol. 233:705-15 (1993).
Chen, et al., Plant Pathol. 40:612-20 (1991).

*Primary Examiner*—Elizabeth McElwain
*Assistant Examiner*—Georgia Helmer
(74) *Attorney, Agent, or Firm*—Lerner, David, Littenberg, Krumholz & Mentlik, LLP

(57) ABSTRACT

Disclosed are recombinant plant cells, plant cell parts, plant parts and transgenic plants containing a DNA molecule comprising a sequence encoding a Pokeweed Antiviral Protein (PAP) II protein. PAP II proteins include full length, wild-type PAP II and substantially nontoxic mutants or analogs including fragments thereof truncated at the C-terminus and other PAP II proteins having an intact catalytic active site amino acid residue E172 but that also have at least one amino acid substitution or deletion, and possess antiviral and/or anti-fungal activity. DNA molecules comprising sequences encoding the mutants or analogs, as well as the isolated and purified PAP II proteins per se, are also disclosed. Methods of identifying nontoxic PAP II mutants are further disclosed.

Transgenic plants that produce a PAP II protein exhibit anti-viral and/or anti-fungal activity. Virtually all flowering plants are included. Seed derived from the transgenic plants are also provided.

29 Claims, 2 Drawing Sheets

```
                                SEQUENCE LISTING

<160> NUMBER OF SEQ ID NOS: 21

<210> SEQ ID NO 1
<211> LENGTH: 1379
<212> TYPE: DNA
<213> ORGANISM: Phytolacca americana
<220> FEATURE:
<221> NAME/KEY: CDS
<222> LOCATION: (225)..(1163)

<400> SEQUENCE: 1
ctatgaagtc gggtcaaagc atatacaggc tatgcattgt tagaaacatt gatgcctctg      60
atcccgataa acaatacaaa ttagacaata agatgacata caagtaccta aactgtgtat     120
gggggagtga aacctcagct gctaaaaaaa cgttgtaaga aaaaaagaaa gttgtgagtt     180
aactacaggg cgaaagtatt ggaactagct agtaggaagg gaag atg aag tcg atg      236
                                                 Met Lys Ser Met
                                                 1 ctt gtg gtg aca ata tca ata tgg ctc att ctt gca cca act tca act      284
Leu Val Val Thr Ile Ser Ile Trp Leu Ile Leu Ala Pro Thr Ser Thr
  5                  10                  15                  20 tgg gct gtg aat aca atc atc tac aat gtt gga agt acc acc att agc      332
Trp Ala Val Asn Thr Ile Ile Tyr Asn Val Gly Ser Thr Thr Ile Ser
                 25                  30                  35 aaa tac gcc act ttt ctg aat gat ctt cgt aat gaa gcg aaa gat cca      380
Lys Tyr Ala Thr Phe Leu Asn Asp Leu Arg Asn Glu Ala Lys Asp Pro
             40                  45                  50 agt tta aaa tgc tat gga ata cca atg ctg ccc aat aca aat aca aat      428
Ser Leu Lys Cys Tyr Gly Ile Pro Met Leu Pro Asn Thr Asn Thr Asn
         55                  60                  65 cca aag tac gtg ttg gtt gag ctc caa ggt tca aat aaa aaa acc atc      476
Pro Lys Tyr Val Leu Val Glu Leu Gln Gly Ser Asn Lys Lys Thr Ile
     70                  75                  80 aca cta atg ctg aga cga aac aat ttg tat gtg atg ggt tat tct gat      524
Thr Leu Met Leu Arg Arg Asn Asn Leu Tyr Val Met Gly Tyr Ser Asp
 85                  90                  95                 100 ccc ttt gaa acc aat aaa tgt cgt tac cat atc ttt aat gat atc tca      572
Pro Phe Glu Thr Asn Lys Cys Arg Tyr His Ile Phe Asn Asp Ile Ser
                105                 110                 115 ggt act gaa cgc caa gat gta gag act act ctt tgc cca aat gcc aat      620
Gly Thr Glu Arg Gln Asp Val Glu Thr Thr Leu Cys Pro Asn Ala Asn
            120                 125                 130 tct cgt gtt agt aaa aac ata aac ttt gat agt cga tat cca aca ttg      668
Ser Arg Val Ser Lys Asn Ile Asn Phe Asp Ser Arg Tyr Pro Thr Leu
        135                 140                 145
```

```
gaa tca aaa gcg gga gta aaa tca aga agt cag gtc caa ctg gga att      716
Glu Ser Lys Ala Gly Val Lys Ser Arg Ser Gln Val Gln Leu Gly Ile
    150                 155                 160 caa ata ctc gac agt aat att gga aag att tct gga gtg atg tca ttc      764
Gln Ile Leu Asp Ser Asn Ile Gly Lys Ile Ser Gly Val Met Ser Phe
165                 170                 175                 180 act gag aaa acc gaa gcc gaa ttc cta ttg gta gcc ata caa atg gta      812
Thr Glu Lys Thr Glu Ala Glu Phe Leu Leu Val Ala Ile Gln Met Val
                185                 190                 195 tca gag gca gca aga ttc aag tac ata gag aat cag gtg aaa act aat      860
Ser Glu Ala Ala Arg Phe Lys Tyr Ile Glu Asn Gln Val Lys Thr Asn
            200                 205                 210 ttt aac aga gca ttc aac cct aat ccc aaa gta ctt aat ttg caa gag      908
Phe Asn Arg Ala Phe Asn Pro Asn Pro Lys Val Leu Asn Leu Gln Glu
        215                 220                 225 aca tgg ggt aag att tca aca gca att cat gat gcc aag aat gga gtt      956
Thr Trp Gly Lys Ile Ser Thr Ala Ile His Asp Ala Lys Asn Gly Val
    230                 235                 240 tta ccc aaa cct ctc gag cta gtg gat gcc agt ggt gcc aag tgg ata     1004
Leu Pro Lys Pro Leu Glu Leu Val Asp Ala Ser Gly Ala Lys Trp Ile
245                 250                 255                 260 gtg ttg aga gtg gat gaa atc aag cct gat gta gca ctc tta aac tac     1052
Val Leu Arg Val Asp Glu Ile Lys Pro Asp Val Ala Leu Leu Asn Tyr
                265                 270                 275 gtt ggt ggg agc tgt cag aca act tat aac caa aat gcc atg ttt cct     1100
Val Gly Gly Ser Cys Gln Thr Thr Tyr Asn Gln Asn Ala Met Phe Pro
            280                 285                 290 caa ctt ata atg tct act tat tat aat tac atg gtt aat ctt ggt gat     1148
Gln Leu Ile Met Ser Thr Tyr Tyr Asn Tyr Met Val Asn Leu Gly Asp
        295                 300                 305 cta ttt gaa gga ttc tgatcataaa cataataagg agtatatata tattactcca     1203
Leu Phe Glu Gly Phe
    310 actatattat aaagcttaaa taagaggccg tgttaattag tacttgttgc cttttgcttt   1263 atggtgttgt ttattatgcc ttgtatgctt gtaatattat ctagagaaca agatgtactg   1323 tgtaatagtc ttgtttgaaa taaaacttcc aattatgatg caaaaaaaaa aaaaaa       1379

<210> SEQ ID NO 2
<211> LENGTH: 313
<212> TYPE: PRT
<213> ORGANISM: Phytolacca americana

<400> SEQUENCE: 2

Met Lys Ser Met Leu Val Val Thr Ile Ser Ile Trp Leu Ile Leu Ala
1               5                   10                  15

Pro Thr Ser Thr Trp Ala Val Asn Thr Ile Ile Tyr Asn Val Gly Ser
            20                  25                  30

Thr Thr Ile Ser Lys Tyr Ala Thr Phe Leu Asn Asp Leu Arg Asn Glu
        35                  40                  45

Ala Lys Asp Pro Ser Leu Lys Cys Tyr Gly Ile Pro Met Leu Pro Asn
    50                  55                  60

Thr Asn Thr Asn Pro Lys Tyr Val Leu Val Glu Leu Gln Gly Ser Asn
65                  70                  75                  80

Lys Lys Thr Ile Thr Leu Met Leu Arg Arg Asn Asn Leu Tyr Val Met
                85                  90                  95

Gly Tyr Ser Asp Pro Phe Glu Thr Asn Lys Cys Arg Tyr His Ile Phe
            100                 105                 110
```

-continued

```
Asn Asp Ile Ser Gly Thr Glu Arg Gln Asp Val Glu Thr Thr Leu Cys
            115                 120                 125

Pro Asn Ala Asn Ser Arg Val Ser Lys Asn Ile Asn Phe Asp Ser Arg
        130                 135                 140

Tyr Pro Thr Leu Glu Ser Lys Ala Gly Val Lys Ser Arg Ser Gln Val
145                 150                 155                 160

Gln Leu Gly Ile Gln Ile Leu Asp Ser Asn Ile Gly Lys Ile Ser Gly
                165                 170                 175

Val Met Ser Phe Thr Glu Lys Thr Glu Ala Glu Phe Leu Leu Val Ala
            180                 185                 190

Ile Gln Met Val Ser Glu Ala Ala Arg Phe Lys Tyr Ile Glu Asn Gln
        195                 200                 205

Val Lys Thr Asn Phe Asn Arg Ala Phe Asn Pro Asn Pro Lys Val Leu
    210                 215                 220

Asn Leu Gln Glu Thr Trp Gly Lys Ile Ser Thr Ala Ile His Asp Ala
225                 230                 235                 240

Lys Asn Gly Val Leu Pro Lys Pro Leu Glu Leu Val Asp Ala Ser Gly
                245                 250                 255

Ala Lys Trp Ile Val Leu Arg Val Asp Glu Ile Lys Pro Asp Val Ala
            260                 265                 270

Leu Leu Asn Tyr Val Gly Gly Ser Cys Gln Thr Thr Tyr Asn Gln Asn
        275                 280                 285

Ala Met Phe Pro Gln Leu Ile Met Ser Thr Tyr Tyr Asn Tyr Met Val
    290                 295                 300

Asn Leu Gly Asp Leu Phe Glu Gly Phe
305                 310

<210> SEQ ID NO 3
<211> LENGTH: 934
<212> TYPE: DNA
<213> ORGANISM: Phytolacca americana
<220> FEATURE:
<221> NAME/KEY: sig_peptide
<222> LOCATION: (1)..(75)
<220> FEATURE:
<221> NAME/KEY: mat_peptide
<222> LOCATION: (76)..(930)
<220> FEATURE:
<221> NAME/KEY: CDS
<222> LOCATION: (1)..(930)

<400> SEQUENCE: 3 atg aag atg aag gtg tta gaa gta gtt ggg ttg gca ata tcg ata tgg      48
Met Lys Met Lys Val Leu Glu Val Val Gly Leu Ala Ile Ser Ile Trp
-25             -20                 -15                 -10 ctg atg ctt aca cca cca gct tct tca aac ata gtg ttt gac gtt gag      96
Leu Met Leu Thr Pro Pro Ala Ser Ser Asn Ile Val Phe Asp Val Glu
            -5                  -1  1                   5 aat gcc aca cca gaa acc tac tct aat ttt ctg act agt ttg cga gaa     144
Asn Ala Thr Pro Glu Thr Tyr Ser Asn Phe Leu Thr Ser Leu Arg Glu
        10                  15                  20 gct gtg aaa gac aag aaa ttg aca tgc cat gga atg ata atg gcc aca     192
Ala Val Lys Asp Lys Lys Leu Thr Cys His Gly Met Ile Met Ala Thr
    25                  30                  35 acc ctc act gaa caa ccc aag tat gtg ttg gtt gac ctc aaa ttc gga     240
Thr Leu Thr Glu Gln Pro Lys Tyr Val Leu Val Asp Leu Lys Phe Gly
40                  45                  50                  55 tct gga aca ttc aca tta gca atc aga agg gga aac tta tat ttg gag     288
Ser Gly Thr Phe Thr Leu Ala Ile Arg Arg Gly Asn Leu Tyr Leu Glu
```

-continued

```
                     60                  65                  70
ggc tat tct gac att tac aat gga aaa tgt cgt tat cgg atc ttc aag        336
Gly Tyr Ser Asp Ile Tyr Asn Gly Lys Cys Arg Tyr Arg Ile Phe Lys
            75                  80                  85 gat tca gaa tcc gat gcc caa gag acc gtt tgc ccc ggg gac aaa agc        384
Asp Ser Glu Ser Asp Ala Gln Glu Thr Val Cys Pro Gly Asp Lys Ser
        90                  95                 100 aag cct ggc act cag aat aat atc ccc tat gaa aag agt tac aaa ggg        432
Lys Pro Gly Thr Gln Asn Asn Ile Pro Tyr Glu Lys Ser Tyr Lys Gly
    105                 110                 115 atg gaa tca aag ggt ggg gct aga act aaa tta ggg tta gga aag ata        480
Met Glu Ser Lys Gly Gly Ala Arg Thr Lys Leu Gly Leu Gly Lys Ile
120                 125                 130                 135 aca ctc aag agt cga atg ggt aaa atc tac ggc aag gat gca acg gat        528
Thr Leu Lys Ser Arg Met Gly Lys Ile Tyr Gly Lys Asp Ala Thr Asp
                140                 145                 150 cag aag cag tat caa aaa aat gag gct gaa ttt ctt ctt ata gcc gtt        576
Gln Lys Gln Tyr Gln Lys Asn Glu Ala Glu Phe Leu Leu Ile Ala Val
            155                 160                 165 caa atg gtt act gag gca tca agg ttc aaa tac att gag aac aaa gtg        624
Gln Met Val Thr Glu Ala Ser Arg Phe Lys Tyr Ile Glu Asn Lys Val
        170                 175                 180 aag gct aaa ttt gat gat gcc aat ggg tat cag cca gat cct aaa gct        672
Lys Ala Lys Phe Asp Asp Ala Asn Gly Tyr Gln Pro Asp Pro Lys Ala
    185                 190                 195 att tcc cta gag aaa aat tgg gac agt gtt tct aag gtc att gca aaa        720
Ile Ser Leu Glu Lys Asn Trp Asp Ser Val Ser Lys Val Ile Ala Lys
200                 205                 210                 215 gtt ggc acc tcc ggt gat agt act gtt act tta cct gga gac cta aaa        768
Val Gly Thr Ser Gly Asp Ser Thr Val Thr Leu Pro Gly Asp Leu Lys
                220                 225                 230 gat gag aat aat aaa cct tgg act acg gcc acc atg aac gac ctt aag        816
Asp Glu Asn Asn Lys Pro Trp Thr Thr Ala Thr Met Asn Asp Leu Lys
            235                 240                 245 aac gac att atg gca ctc cta acc cac gtt act tgc aag gtt aaa agt        864
Asn Asp Ile Met Ala Leu Leu Thr His Val Thr Cys Lys Val Lys Ser
        250                 255                 260 tcc atg ttc cct gaa att atg tcc tat tat tat agg act agt att agt        912
Ser Met Phe Pro Glu Ile Met Ser Tyr Tyr Tyr Arg Thr Ser Ile Ser
    265                 270                 275 aac ctt ggt gaa ttc gag tgat                                           934
Asn Leu Gly Glu Phe Glu
280                 285
```

<210> SEQ ID NO 4
<211> LENGTH: 310
<212> TYPE: PRT
<213> ORGANISM: Phytolacca americana

<400> SEQUENCE: 4

```
Met Lys Met Lys Val Leu Glu Val Val Gly Leu Ala Ile Ser Ile Trp
-25                 -20                 -15                 -10

Leu Met Leu Thr Pro Ala Ser Ser Asn Ile Val Phe Asp Val Glu
                -5                  -1   1                   5

Asn Ala Thr Pro Glu Thr Tyr Ser Asn Phe Leu Thr Ser Leu Arg Glu
            10                  15                  20

Ala Val Lys Asp Lys Lys Leu Thr Cys His Gly Met Ile Met Ala Thr
        25                  30                  35

Thr Leu Thr Glu Gln Pro Lys Tyr Val Leu Val Asp Leu Lys Phe Gly
```

```
              40                  45                  50                  55
Ser Gly Thr Phe Thr Leu Ala Ile Arg Arg Gly Asn Leu Tyr Leu Glu
                    60                  65                  70

Gly Tyr Ser Asp Ile Tyr Asn Gly Lys Cys Arg Tyr Arg Ile Phe Lys
            75                  80                  85

Asp Ser Glu Ser Asp Ala Gln Glu Thr Val Cys Pro Gly Asp Lys Ser
        90                  95                 100

Lys Pro Gly Thr Gln Asn Asn Ile Pro Tyr Glu Lys Ser Tyr Lys Gly
   105                 110                 115

Met Glu Ser Lys Gly Gly Ala Arg Thr Lys Leu Gly Leu Gly Lys Ile
120                 125                 130                 135

Thr Leu Lys Ser Arg Met Gly Lys Ile Tyr Gly Lys Asp Ala Thr Asp
                140                 145                 150

Gln Lys Gln Tyr Gln Lys Asn Glu Ala Glu Phe Leu Leu Ile Ala Val
            155                 160                 165

Gln Met Val Thr Glu Ala Ser Arg Phe Lys Tyr Ile Glu Asn Lys Val
        170                 175                 180

Lys Ala Lys Phe Asp Asp Ala Asn Gly Tyr Gln Pro Asp Pro Lys Ala
    185                 190                 195

Ile Ser Leu Glu Lys Asn Trp Asp Ser Val Ser Lys Val Ile Ala Lys
200                 205                 210                 215

Val Gly Thr Ser Gly Asp Ser Thr Val Thr Leu Pro Gly Asp Leu Lys
                220                 225                 230

Asp Glu Asn Asn Lys Pro Trp Thr Thr Ala Thr Met Asn Asp Leu Lys
            235                 240                 245

Asn Asp Ile Met Ala Leu Leu Thr His Val Thr Cys Lys Val Lys Ser
        250                 255                 260

Ser Met Phe Pro Glu Ile Met Ser Tyr Tyr Tyr Arg Thr Ser Ile Ser
    265                 270                 275

Asn Leu Gly Glu Phe Glu
280                 285

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
gggttgttca gtgagggttg tggcc                                            25

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 6
tttggaggac tattctgac                                                   19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Primer
```

```
<400> SEQUENCE: 7
gtcagaatag tcctccaaa                                               19

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 8
ccgttcaaat ggttactgtg gcatcaaggt tc                                32

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 9
gaaccttgat gccacagtaa ccatttgaac gg                                32

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
aaaccttaga ctacggccac                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
gtggccgtag tctaaggttt                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
aaacctagga ctacggccac                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
gtggccgtag tcctaggttt                                              20

<210> SEQ ID NO 14
```

-continued

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
cgacattatg gcagccctaa cccacgttac					30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 15
gtaacgtggg ttagggctgc cataatgtcg					30

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 16
cgacattatg gcactccgaa cccacgttac ttgc				34

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 17
gcaagtaacg tgggttcgga gtgccataat gtcg				34

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 18
cacgttactt gctaggttaa aagttccatg ttcc				34

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 19
ggaacatgga acttttaacc tagcaagtaa cgtg				34

<210> SEQ ID NO 20
<211> LENGTH: 855
<212> TYPE: DNA
<213> ORGANISM: Phytolacca americana
<220> FEATURE:
<221> NAME/KEY: CDS
<222> LOCATION: (1)..(855)

```
<400> SEQUENCE: 20 aac ata gtg ttt gac gtt gag aat gcc aca cca gaa acc tac tct aat       48
Asn Ile Val Phe Asp Val Glu Asn Ala Thr Pro Glu Thr Tyr Ser Asn
 1               5                  10                  15 ttt ctg act agt ttg cga gaa gct gtg aaa gac aag aaa ttg aca tgc       96
Phe Leu Thr Ser Leu Arg Glu Ala Val Lys Asp Lys Lys Leu Thr Cys
             20                  25                  30 cat gga atg ata atg gcc aca acc ctc act gaa caa ccc aag tat gtg      144
His Gly Met Ile Met Ala Thr Thr Leu Thr Glu Gln Pro Lys Tyr Val
         35                  40                  45 ttg gtt gac ctc aaa ttc gga tct gga aca ttc aca tta gca atc aga      192
Leu Val Asp Leu Lys Phe Gly Ser Gly Thr Phe Thr Leu Ala Ile Arg
     50                  55                  60 agg gga aac tta tat ttg gag ggc tat tct gac att tac aat gga aaa      240
Arg Gly Asn Leu Tyr Leu Glu Gly Tyr Ser Asp Ile Tyr Asn Gly Lys
 65                  70                  75                  80 tgt cgt tat cgg atc ttc aag gat tca gaa tcc gat gcc caa gag acc      288
Cys Arg Tyr Arg Ile Phe Lys Asp Ser Glu Ser Asp Ala Gln Glu Thr
                 85                  90                  95 gtt tgc ccc ggg gac aaa agc aag cct ggc act cag aat aat atc ccc      336
Val Cys Pro Gly Asp Lys Ser Lys Pro Gly Thr Gln Asn Asn Ile Pro
            100                 105                 110 tat gaa aag agt tac aaa ggg atg gaa tca aag ggt ggg gct aga act      384
Tyr Glu Lys Ser Tyr Lys Gly Met Glu Ser Lys Gly Gly Ala Arg Thr
        115                 120                 125 aaa tta ggg tta gga aag ata aca ctc aag agt cga atg ggt aaa atc      432
Lys Leu Gly Leu Gly Lys Ile Thr Leu Lys Ser Arg Met Gly Lys Ile
    130                 135                 140 tac ggc aag gat gca acg gat cag aag cag tat caa aaa aat gag gct      480
Tyr Gly Lys Asp Ala Thr Asp Gln Lys Gln Tyr Gln Lys Asn Glu Ala
145                 150                 155                 160 gaa ttt ctt ctt ata gcc gtt caa atg gtt act gag gca tca agg ttc      528
Glu Phe Leu Leu Ile Ala Val Gln Met Val Thr Glu Ala Ser Arg Phe
                165                 170                 175 aaa tac att gag aac aaa gtg aag gct aaa ttt gat gat gcc aat ggg      576
Lys Tyr Ile Glu Asn Lys Val Lys Ala Lys Phe Asp Asp Ala Asn Gly
            180                 185                 190 tat cag cca gat cct aaa gct att tcc cta gag aaa aat tgg gac agt      624
Tyr Gln Pro Asp Pro Lys Ala Ile Ser Leu Glu Lys Asn Trp Asp Ser
        195                 200                 205 gtt tct aag gtc att gca aaa gtt ggc acc tcc ggt gat agt act gtt      672
Val Ser Lys Val Ile Ala Lys Val Gly Thr Ser Gly Asp Ser Thr Val
    210                 215                 220 act tta cct gga gac cta aaa gat gag aat aat aaa cct tgg act acg      720
Thr Leu Pro Gly Asp Leu Lys Asp Glu Asn Asn Lys Pro Trp Thr Thr
225                 230                 235                 240 gcc acc atg aac gac ctt aag aac gac att atg gca ctc cta acc cac      768
Ala Thr Met Asn Asp Leu Lys Asn Asp Ile Met Ala Leu Leu Thr His
                245                 250                 255 gtt act tgc aag gtt aaa agt tcc atg ttc cct gaa att atg tcc tat      816
Val Thr Cys Lys Val Lys Ser Ser Met Phe Pro Glu Ile Met Ser Tyr
            260                 265                 270 tat tat agg act agt att agt aac ctt ggt gaa ttc gag                  855
Tyr Tyr Arg Thr Ser Ile Ser Asn Leu Gly Glu Phe Glu
        275                 280                 285

<210> SEQ ID NO 21
<211> LENGTH: 285
<212> TYPE: PRT
<213> ORGANISM: Phytolacca americana
```

<400> SEQUENCE: 21

```
Asn Ile Val Phe Asp Val Glu Asn Ala Thr Pro Glu Thr Tyr Ser Asn
 1               5                  10                  15
Phe Leu Thr Ser Leu Arg Glu Ala Val Lys Asp Lys Lys Leu Thr Cys
             20                  25                  30
His Gly Met Ile Met Ala Thr Thr Leu Thr Glu Gln Pro Lys Tyr Val
         35                  40                  45
Leu Val Asp Leu Lys Phe Gly Ser Gly Thr Phe Thr Leu Ala Ile Arg
     50                  55                  60
Arg Gly Asn Leu Tyr Leu Glu Gly Tyr Ser Asp Ile Tyr Asn Gly Lys
 65                  70                  75                  80
Cys Arg Tyr Arg Ile Phe Lys Asp Ser Glu Ser Asp Ala Gln Glu Thr
                 85                  90                  95
Val Cys Pro Gly Asp Lys Ser Lys Pro Gly Thr Gln Asn Asn Ile Pro
             100                 105                 110
Tyr Glu Lys Ser Tyr Lys Gly Met Glu Ser Lys Gly Gly Ala Arg Thr
         115                 120                 125
Lys Leu Gly Leu Gly Lys Ile Thr Leu Lys Ser Arg Met Gly Lys Ile
    130                 135                 140
Tyr Gly Lys Asp Ala Thr Asp Gln Lys Gln Tyr Gln Lys Asn Glu Ala
145                 150                 155                 160
Glu Phe Leu Leu Ile Ala Val Gln Met Val Thr Glu Ala Ser Arg Phe
                165                 170                 175
Lys Tyr Ile Glu Asn Lys Val Lys Ala Lys Phe Asp Asp Ala Asn Gly
            180                 185                 190
Tyr Gln Pro Asp Pro Lys Ala Ile Ser Leu Glu Lys Asn Trp Asp Ser
        195                 200                 205
Val Ser Lys Val Ile Ala Lys Val Gly Thr Ser Gly Asp Ser Thr Val
    210                 215                 220
Thr Leu Pro Gly Asp Leu Lys Asp Glu Asn Asn Lys Pro Trp Thr Thr
225                 230                 235                 240
Ala Thr Met Asn Asp Leu Lys Asn Asp Ile Met Ala Leu Leu Thr His
                245                 250                 255
Val Thr Cys Lys Val Lys Ser Ser Met Phe Pro Glu Ile Met Ser Tyr
            260                 265                 270
Tyr Tyr Arg Thr Ser Ile Ser Asn Leu Gly Glu Phe Glu
        275                 280                 285
```

TRANSGENIC PLANTS PRODUCING A PAP II PROTEIN

CROSS-REFERENCE TO RELATED APPLICATIONS

This application is a continuation of PCT/US99/11301, filed May 21, 1999, which claims the benefit of the filing date of U.S. Provisional Application No. 60/086,374, filed May 22, 1998, the disclosure of which is hereby incorporated herein by reference.

GOVERNMENTAL SUPPORT

Work on the invention described herein was supported in part by National Science Foundation Grant MCB 96-31308. Therefore, the Government may have certain rights in the invention.

TECHNICAL FIELD

This invention relates generally to agricultural biotechnology, and more specifically to methods and genetic materials for conferring resistance to viruses and/or fungi in plants.

BACKGROUND ART

Many commercially valuable agricultural crops are prone to infection by plant viruses. These viruses are capable of inflicting significant damage to a crop in a given season, and thus can drastically reduce its economic value. The reduction in economic value to the farmer in turn results in a higher cost of goods to ultimate purchasers. Several published studies have been directed to the expression of plant virus capsid proteins in a plant in an effort to confer resistance to viruses. See, e.g., Abel, et al., Science 232: 738–743 (1986); Cuozzo, et al., Bio/Technology 6:549–557 (1988); Hemenway, et al., EMBO J. 7:1273–1280 (1988); Stark, et al., Bio/Technology 7:1257–1262 (1989); and Lawson, et al., Bio/Technology 8:127–134 (1990). The transgenic plants exhibited resistance only to the homologous virus and related viruses, however, and not to unrelated viruses. Kawchuk, et al., Mol. Plant-Microbe Interactions 3 (5):301–307 (1990), disclose the expression of wild-type potato leafroll virus (PLRV) coat protein gene in potato plants. Although the infected plants exhibited resistance to PLRV, all of the transgenic plants that were inoculated with PLRV became infected with the virus and thus allowed for the continued transmission of the virus such that high levels of resistance could not be expected. See U.S. Pat. No. 5,304,730.

Lodge, et al., Proc. Natl. Acad. Sci. USA 90:7089–7093 (1993), report the *Agrobacterium tumefaciens*-mediated transformation of tobacco with a cDNA encoding wild-type pokeweed antiviral protein (PAP) and the resistance of the transgenic tobacco plants to unrelated viruses. PAP is a Type I ribosome-inhibiting protein (RIP) found in the cell walls of *Phytolacca americana* (pokeweed). It is a single polypeptide chain that catalytically removes a specific adenine residue from a highly conserved stem-loop structure in the 28S rRNA of eukaryotic ribosomes, thus interfering with Elongation Factor-2 binding and blocking cellular protein synthesis. See, e.g. Irvin, et al., Pharmac. Ther. 55:279–302 (1992); Endo, et al., Biophys. Res. Comm., 150:1032–1036 (1988); and Hartley, et al., FEBS Lett. 290:65–68 (1991).

The observations in Lodge are in sharp contrast to previous studies reporting that transgenic plants expressing a viral gene were resistant to that virus and closely related viruses only. See also Beachy, et al., Ann. Rev. Phytopathol. 28:451–474 (1990); and Golemboski, et al., Proc. Natl. Acad. Sci. USA 87:6311–6315 (1990). Lodge also reports, however, that the PAP-expressing tobacco plants (i.e., above 10 ng/mg protein) tended to have a stunted, mottled phenotype, and that other transgenic tobacco plants that accumulated the highest levels of PAP were sterile.

Hence, a need remains for a means by which to confer broad spectrum virus resistance to plants which overcomes the problems associated with known methods, and particularly which would require a minimum number of transgenes, the expression of which would not cause plant cell death or sterility.

SUMMARY OF THE INVENTION

A first aspect of the present invention is directed to a recombinant plant cell or part thereof e.g. a protoplast, containing a DNA molecule comprising a sequence encoding a PAP II protein. PAP II proteins include full length, wild-type PAP II, fragments thereof truncated at the C-terminus and other mutants or analogs having at least one amino acid substitution or deletion, but which have an intact catalytic active site amino acid residue E172. The PAP II proteins confer anti-viral and/or anti-fungal properties to plants. DNA molecules comprising sequences encoding the fragments and mutants or analogs, as well as the isolated and purified PAP II proteins per se, are also provided.

Another aspect of the present invention is directed to transgenic plants that produce a PAP II protein, and exhibit anti-viral and/or anti-fungal activity. Plant parts e.g., leaves, stems and shoots, containing a DNA molecule comprising a sequence encoding a sequence encoding a PAP II protein, from which whole plants expressing the DNA can be regenerated, are also provided. Virtually all flowering plants are included. Seed derived from the transgenic plants are also provided.

A further aspect of the present invention is directed to a method for identifying PAP II proteins having substantially no cytotoxicity (e.g., phytotoxicity). The method entails providing a transformed eukaryotic cell transformed with a mutagenized PAP II protein-encoding DNA molecule. The transformed cell is cultured in medium containing an inducer to cause expression of the DNA molecule. The toxicity of the PAP II protein encoded by the DNA is determined by whether the cultured cell survives in the presence of the PAP II protein.

BEST MODE OF CARRYING OUT INVENTION

Figure 1:
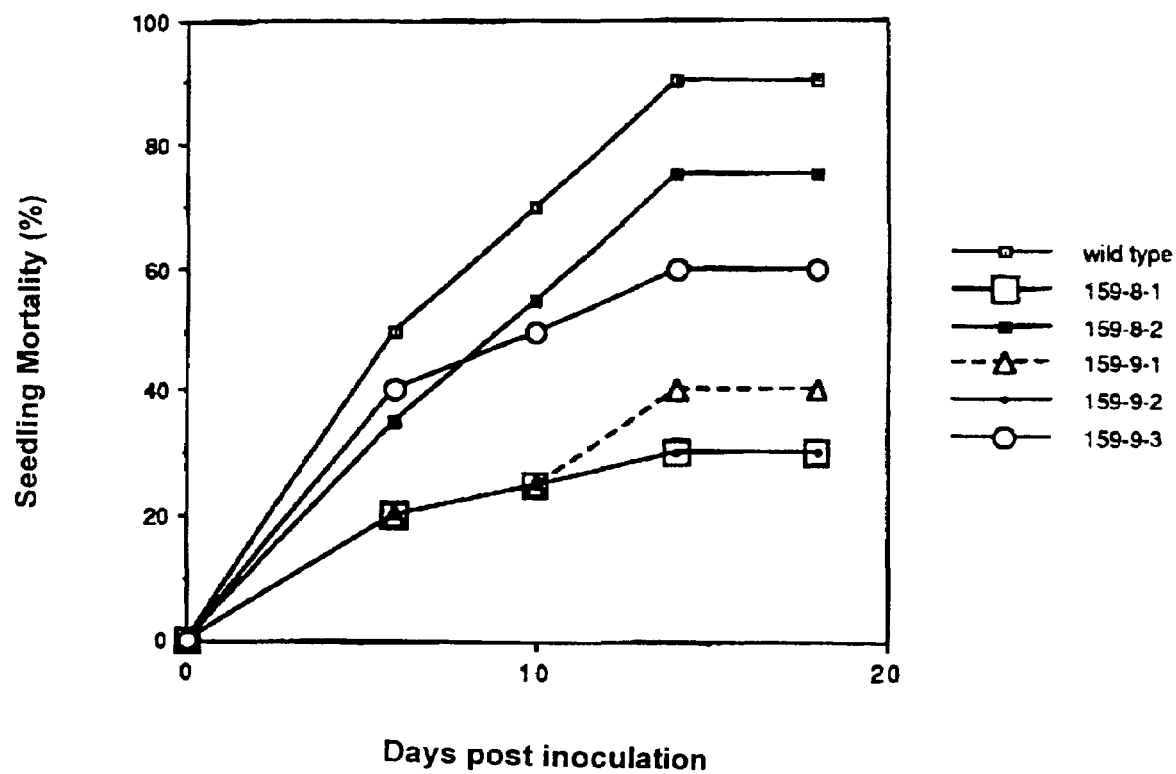
FIG. 1 is a graph showing susceptibility of transgenic plants expressing PAP II to *Rhizoctonia solani*.

Transgenic plants expressing DNAs encoding a PAP II protein exhibit anti-viral and/or anti-fungal activities with substantially reduced phytotoxicity compared to transgenic plants that produce PAP ("PAP I"). Thus, transgenic plants that express a heterologous PAP II DNA exhibit a normal and fertile phenotype as opposed to the stunted, mottled phenotype characteristic of transgenic plants that produce mature PAP, particularly at relatively high levels (as disclosed in Lodge, et al., Proc. Natl. Acad. Sci. USA 90:7089–7093 (1993)).

By "wild-type PAP," it is meant the PAP amino acid sequence 1–262, the 22-amino acid N-terminal signal peptide ("the N-terminal signal sequence of wild-type PAP"), and the 29 amino acid C-terminal extension (amino acids enumerated 263–291), all illustrated in Table 1 below as SEQ ID NO:2. The corresponding nucleotide sequence is set forth as SEQ ID NO:1. Thus, by the terms "wild-type, mature PAP," or "mature PAP", it is meant the PAP amino acid sequence 1–262 shown in Table 1.

TABLE 1

```
5'CTATGAAGTCGGGTCAAAGCATATACAGGCTATGCATTGTTAGAAACATTGATGCCTCTGATCC
CGATAAACAATACAAATTAGACAATAAGATGACATACAAGTACCTAAACTCTGTATGGGGAGT
GAAACCTCAGCTGCTAAAAAAACGTTGTAAGAAAAAAAGAAAGTTGTGAGTTAACTACAGGGCG
AAAGTATTGGAACT
AGCTAGTAGGAAGGGAAG ATG AAG TCG ATG CTT GTG GTG ACA ATA TCA ATA
                   Met Lys Ser Met Leu Val Val Thr Ile Ser Ile
                                                          (67)
TGG CTC ATT CTT GCA CCA ACT TCA ACT TGG GCT GTG AAT ACA ATC ATC TAC
Trp Leu Ile Leu Ala Pro Thr Ser Thr Trp Ala Val Asn Thr Ile Ile Tyr
                                                (1)
              (100)
AAT GTT GGA AGT ACC ACC ATT AGC AAA TAC GCC ACT TTT CTG AAT CAT CTT
Asn Val Gly Ser Thr Thr Ile Ser Lys Tyr Ala Thr Phe Leu Asn Asp Leu
            (10)                                            (20)
CGT AAT GAA GCG AAA GAT CCA AGT TTA AAA TGC TAT GGA ATA CCA ATG CTG
Arg Asn Glu Ala Lys Asp Pro Ser Leu Lys Cys Tyr Gly Ile Pro Met Leu
                        (30)                                    (40)
CCC AAT ACA AAT ACA AAT CCA AAG TAC GTG TTG GTT GAG CTC CAA GGT TCA
Pro Asn Thr Asn Thr Asn Pro Lys Tyr Val Leu Val Glu Leu Gln Gly Ser
                                (50)
AAT AAA AAA ACC ATC ACA CTA ATG CTG AGA CGA AAC AAT TTG TAT GTG ATG
Asn Lys Lys Thr Ile Thr Leu Met Leu Arg Arg Asn Asn Leu Tyr Val Met
                (60)                                (70)
GGT TAT TCT GAT CCC TTT GAA ACC AAT AAA TGT CGT TAC CAT ATC TTT AAT
Gly Tyr Ser Asp Pro Phe Glu Thr Asn Lys Cys Arg Tyr His Ile Phe Asn
                    (80)                                        (90)
GAT ATC TCA GGT ACT GAA CGC CAA GAT GTA GAG ACT ACT CTT TGC CCA AAT
Asp Ile Ser Gly Thr Glu Arg Gln Asp Val Glu Thr Thr Leu Cys Pro Asn
                            (100)
GCC AAT TCT CCT GTT AGT AAA AAC ATA AAC TTT GAT AGT CGA TAT CCA ACA
Ala Asn Ser Arg Val Ser Lys Asn Ile Asn Phe Asp Ser Arg Tyr Pro Thr
        (110)                                   (120)
TTG GAA TCA AAA GCG GGA GTA AAA TCA AGA AGT CAG GTC CAA CTG GGA ATT
Leu Glu Ser Lys Ala Gly Val Lys Ser Arg Ser Gln Val Gln Leu Gly Ile
                    (130)                                   (140)
CAA ATA CTC GAC AGT AAT ATT GGA AAG ATT TCT GGA GTG ATG TCA TTC ACT
Gln Ile Leu Asp Ser Asn Ile Gly Lys Ile Ser Gly Val Met Ser Phe Thr
                            (150)
GAG AAA ACC GAA GCC GAA TTC CTA TTG GTA GCC ATA CAA ATG GTA TCA GAG
Glu Lys Thr Glu Ala Glu Phe Leu Leu Val Ala Ile Gln Met Val Ser Glu
(160)                                       (170)
GCA GCA AGA TTC AAG TAC ATA GAG AAT CAG GTG AAA ACT AAT TTT AAC AGA
Ala Ala Arg Phe Lys Tyr Ile Glu Asn Gln Val Lys Thr Asn Phe Asn Arg
            (180)                                       (190)
GCA TTC AAC CCT AAT CCC AAA GTA CTT AAT TTG CAA GAG ACA TGG GGT AAG
Ala Phe Asn Pro Asn Pro Lys Val Leu Asn Leu Gln Glu Thr Trp Gly Lys
                        (200)                                   (210)
ATT TCA ACA GCA ATT CAT GAT GCC AAG AAT GGA GTT TTA CCC AAA CCT CTC
Ile Ser Thr Ala Ile His Asp Ala Lys Asn Gly Val Leu Pro Lys Pro Leu
                                (220)
GAG CTA GTG GAT GCC AGT GGT GCC AAG TGG ATA GTG TTG AGA GTG GAT GAA
Glu Leu Val Asp Ala Ser Gly Ala Lys Trp Ile Val Leu Arg Val Asp Glu
        (230)                                   (240)
ATC AAG CCT GAT GTA GCA CTC TTA AAC TAC GTT GGT GGG AGC TGT CAG ACA
Ile Lys Pro Asp Val Ala Leu Leu Asn Tyr Val Gly Gly Ser Cys Gln Thr
                    (250)                                   (260)
ACT TAT AAC CAA AAT GCC ATG TTT CCT CAA CTT ATA ATG TCT ACT TAT TAT
Thr Tyr Asn Gln Asn Ala Met Phe Pro Gln Leu Ile Met Ser Thr Tyr Tyr
(262)                           (270)
AAT TAC ATG GTT AAT CTT GGT GAT CTA TTT GAA GGA TTC TGATCATAAACA
Asn Tyr Met Val Asn Leu Gly Asp Leu Phe Glu Gly Phe (SEQ ID NO:2)
    (280)                                   (290)
TAATAAGGAGTATATATATATTACTCCAACTATATTATAAAGCTTAAATAAGAGGCCGTGTTAAT
TAGTACTTGTTGCCTTTTGCTTTATGGTGTTGTTTATTATGCCTTGTATGCTTGTAATATTATCTAG
AGAACAAGATGTACTGTGTAATAGTCTTGTTTGAAATAAAACTTCCAATTATGATGCAAAAAAAA
AAAAAAA3' (SEQ ID NO:1)
```

Table 1 also shows 5' and 3' non-coding, flanking sequences. Upon expression in eukaryotic cells, the N-terminal 22-amino acid sequence of wild-type PAP is co-translationally cleaved, yielding a polypeptide having a molecular weight of about 32 kD, which is then further processed by the cleavage of the C-terminal 29-amino acids ("the C-terminal extension of wild-type PAP" or "PAP (263-292)"), yielding mature, wild-type PAP (hereinafter "PAP (1-262)") (i.e., that which is isolated from *Phytolacca americana* leaves), having a molecular weight of about 29 kD. See Irvin, et al., Pharmac. Ther. 55:279–302 (1992); Dore, et al., Nuc. Acids Res. 21 (18):4200–4205 (1993); Monzingo, et al., J. Mol. Biol. 233:705–715 (1993); and Turner, et al., Proc. Natl. Acad. Sci. USA 92:8448–8452 (1995).

The term "PAP-II protein" is meant to include the 310 amino acid "immature" wild-type polypeptide disclosed in Poyet, et al., FEBS letters 347:268–272 (1994) and the 285-amino acid polypeptide containing amino acid residues 26–310 of the immature polypeptide (i.e. "PAP II (1-285)" or "mature PAP II" that excludes the N-terminal twenty-five-amino acid signal sequence). The nucleotide sequence and corresponding amino acid sequence of immature wild-type PAP II are set forth in Table 2. They are denoted as SEQ ID NOS:3 and 4 respectively (wherein the 25-amino acid signal sequence is shown using negative numbering). The nucleotide sequence and corresponding amino acid sequence of mature wild-type PAP II are denoted as SEQ ID NOS:20 and 21 respectively.

TAELE 2

PAPII

```
         ATGAAGATGAAGGTGTTAGAAGTAGTTGGGTTGGCAATATCGATATGGCTGATGCTTACA
  55     -----+----------+----------+----------+----------+-----------+----114
         TACTTCTACTTCCACAATCTTCATCAACCCAACCGTTATAGCTATACCGACTACGAATGT
          M  K  M  K  V  L  E  V  V  G  L  A  I  S  I  W  L  M  L  T   -
         CCACCAGCTTCTTCAAACATAGTGTTTGACGTTGAGAATGCCACACCAGAAACCTACTCT
 115     -----+----------+----------+----------+----------+-----------+----174
         GGTGGTCGAAGAAGTTTGTATCACAAACTGCAACTCTTACGGTGTGGTCTTTGGATGAGA
          P  P  A  S  S  N  I  V  F  D  V  K  E  A  T  P  E  T  Y  S   -
         AATTTTCTGACTAGTTTGCGAGAAGCTGTGAAAGACAAGAAATTGACATGCCATGGAATG
 175     -----+----------+----------+----------+----------+-----------+----234
         TTAAAAGACTGATCAAACGCTCTTCGACACTTTCTGTTCTTTAACTGTACGGTACCTTAC
          N  F  L  T  S  L  R  E  A  V  K  D  K  K  L  T  C  H  G  M   -
         ATAATGGCCACAACCCTCACTGAACACCCAAGTATGTGTTGGTTGACCTCAAATTCGGA
 235     -----+----------+----------+----------+----------+-----------+----294
         TATTACCGGTGTTGGGAGTGACTTGTTGGGTTCATACACAACCAACTGGAGTTTAAGCCT
          I  M  A  T  T  L  T  E  Q  P  K  Y  V  L  V  D  L  K  F  G   -
         TCTGGAACATTCACATTAGCAATCAGAAGGGGAAACTTATATTTGGAGGGCTATTCTGAC
 295     -----+----------+----------+----------+----------+-----------+----354
         AGACCTTGTAAGTGTAATCGTTAGTCTTCCCCTTTGAATATAAACCTCCCGATAAGACTG
          S  G  T  F  T  L  A  I  R  R  G  N  L  Y  L  E  G  Y  S  D   -
         ATTTTACAATGGAAAATGTCGTTATCGGATCTTCAAGGATTCAGAATCCGATGCCCAAGAG
 355     -----+----------+----------+----------+----------+-----------+----414
         TAAATGTTACCTTTTACAGCAATAGCCTAGAAGTTCCTAAGTCTTAGGCTACGGGTTCTC
          I  Y  N  G  K  C  R  Y  R  I  F  K  D  S  E  S  D  A  Q  E   -
         ACCGTTTGCCCCGGGGACAAAAGCAAGCCTGGCACTCAGAATAATATCCCCTATGAAAAG
 415     -----+----------+----------+----------+----------+-----------+----474
         TGGCAAACGGGGCCCCTGTTTTCGTTCGGACCGTGAGTCTTATTATAGGGGATACTTTTC
          T  V  C  P  G  D  K  S  K  P  G  T  O  N  N  I  P  Y  E  K   -
         AGTTACAAAGGGATGGAATCAAAGGGTGGGGCTAGAACTAAATTAGGGTTAGGAAAGATA
 475     -----+----------+----------+----------+----------+-----------+----534
         TCAATGTTTCCCTACCTTAGTTTCCCACCCCGATCTTGATTTAATCCCAATCCTTTCTAT
          S  Y  K  G  M  E  S  K  G  G  A  R  T  K  L  G  L  G  K  I   -
         ACACTCAAGAGTCGAATGGGTAAAATCTACGGCAAGGATGCAACGGATCAGAAGCAGTAT
 535     -----+----------+----------+----------+----------+-----------+----594
         TGTGAGTTCTCAGCTTACCCATTTTAGATGCCGTTCCTACGTTGCCTAGTCTTCGTCATA
          T  L  K  S  R  M  G  K  I  Y  G  K  D  A  T  D  Q  K  Q  Y   -
         CAAAAAAATGAGGCTGAATTTCTTCTTATAGCCGTTCAAATGGTTACTGAGGCATCAAGG
 595     -----+----------+----------+----------+----------+-----------+----654
         GTTTTTTTACTCCGACTTAAAGAAGAATATCGGCAAGTTTACCAATGACTCCGTAGTTCC
          Q  K  N  E  A  E  F  L  L  I  A  V  Q  M  V  T  E  A  S  R   -
         TTCAAATACATTGAGAACAAAGTGAAGGCTAAATTTGATGATGCCAATGGGTATCAGCCA
 655     -----+----------+----------+----------+----------+-----------+----714
         AAGTTTATGTAACTCTTGTTTCACTTCCGATTTAAACTACTACGGTTACCCATAGTCGGT
          F  K  Y  I  E  N  K  V  A  K  F  D  D  A  N  G  Y  Q  P   -
         GATCCTAAAGCTATTTCCCTAGAGAAAAATTGGGACAGTGTTTCTAAGGTCATTGCAAAA
 715     -----+----------+----------+----------+----------+-----------+----774
         CTAGGATTTCGATAAAGGGATCTCTTTTTAACCCTGTCACAAAGATTCCAGTAACGTTTT
          D  P  K  A  I  S  L  E  K  N  W  D  S  V  S  K  V  I  A  K   -
         GTTGGCACCTCCGGTGATAGTACTGTTACTTTACCTGGAGACCTAAAAGATGAGAATAAT
 775     -----+----------+----------+----------+----------+-----------+----834
         CAACCGTGGAGGCCACTATCATGACAATGAAATGGACCTCTGGATTTTCTACTCTTATTA
          V  G  T  S  G  D  S  T  V  T  L  P  G  D  L  K  D  E  N  N   -
         AAACCTTGGACTACGGCCACCATGAACGACCTTAAGAACGACATTATGGCACTCCTAACC
 835     -----+----------+----------+----------+----------+-----------+----894
         TTTGGAACCTGATGCCGGTGGTACTTGCTGGAATTCTTGCTGTAATACCGTGAGGATTGG
          K  P  W  T  T  A  T  M  N  D  L  K  N  D  I  M  A  L  L  T   -
         CACGTTACTTGCAAGGTTAAAAGTTCCATGTTCCCTGAAATTATGTCCTATTATTATAGG
```

TAELE 2-continued

PAPII

```
895 -----+----------+----------+----------+----------+----------+----954
    GTGCAATGAACGTTCCAATTTTCAAGGTACAAGGGACTTTAATACAGGATAATAATATCC
     H  V  T  C  K  V  K  S  S  M  F  P  E  I  M  S  Y  Y  Y  R   -
    ACTAGTATTAGTAACCTTGGTGAATTCGAGTGAT
955 -----+----------+----------+-------- 988
    TGATCATAATCATTGGAACCACTTAAGCTCACTA      (SEQ ID NO:3)
     T  S  I  S  N  L  G  E  F  E  *    -  (SEQ ID NO:4)
```

The term "PAP II protein" is also meant to include mutants or analogs of the wild-type polypeptide such as fragments (e.g. C-terminal deletions) and amino acid substitutions and/or deletions. The non-wild type polypeptides contain the wild-type E172 amino acid residue (see, Poyet, et al., Biochem. Biophys. Res. Comm. 259:582–587 (1998)) and substantially retain PAP II properties as described herein. Without intending to be bound by any particular theory of operation, Applicants believe that this amino acid residue is necessary for anti-viral and/or anti-fungal activity. Preferred non-wild type PAP II proteins include PAP II (1-285, G72D), PAP II (1-285, L254R), PAP II (1-285, L254A), PAP II (1-237), PAP II (1-238), PAP II (1-239), PAP II (1-240), PAP II (1-241), PAP II (1-242), PAP II (1-243), PAP II (1-244), PAP II (1-245), PAP II (1-246), PAP II (1-247), PAP II (1-248), PAP II (1-249), PAP II (1-250), PAP II (1-251), PAP II (1-252), PAP II (1-253), PAP II (1-254), PAP II (1-255), PAP II (1-256), PAP II (1-257), PAP II (1-258) and PAP II (1-259). PAP II proteins may be prepared by preparing hosts transformed with the DNAs, culturing the transformed hosts, and isolating the expression product, all in accordance with standard techniques.

Figure 2:
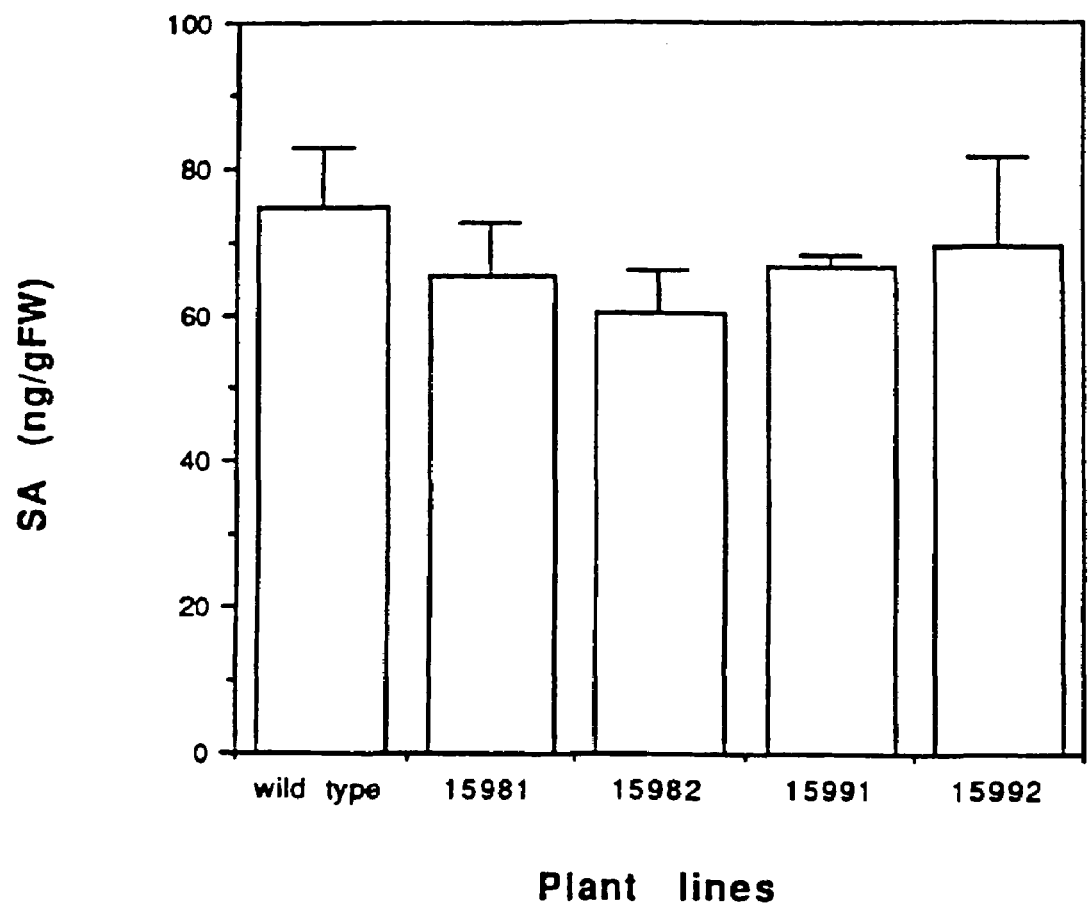
FIG. 2 is a bar graph showing salicyclic acid levels in transformed *N. Tabacum* cv Samsun plants expressing PAP II and in untransformed plants.

FIG. 2 of Poyet, et al., (1998) illustrates that PAP and PAP II amino acid sequences share 33% sequence similarity. Applicants have demonstrated 41% sequence similarity. There is much greater similarity between the active sites of these respective polypeptides, however. That is, the active sites are substantially conserved. Thus, it would have been expected that the cytotoxicity of PAP II was roughly equal to that of PAP, despite the lack of high overall sequence similarity.

PAP II exhibits anti-viral activity. Expression of a PAP II protein in a transgenic plant confers broad spectrum virus resistance, i.e., resistance to or the capability of suppressing infection by a number of unrelated viruses, including but not limited to RNA viruses e.g., potexviruses such as (PVX, potato virus X), potyvirus (PVY), cucumber mosaic virus (CMV), tobacco mosaic viruses (TMV), barley yellow dwarf virus (BYDV), wheat streak mosaic virus, potato leaf roll virus (PLRV), plumpox virus, watermelon mosaic virus, zucchini yellow mosaic virus, papaya ringspot virus, beet western yellow virus, soybean dwarf virus, carrot read leaf virus and DNA plant viruses such as tomato yellow leaf curl virus. See also Lodge, et al., supra., Tomlinson, et al., J. Gen. Virol. 22:225-232 (1974); and Chen, et al., Plant Pathol. 40:612-620 (1991).

PAP II also exhibits anti-fungal activity. PAP II proteins confer broad spectrum fungal resistance to plants. PAP II provides increased resistance to diseases caused by plant fungi, including those caused by *Pythium* (one of the causes of seed rot, seedling damping off and root rot), *Phytophthora* (the cause of late blight of potato and of root rots, and blights of many other plants), *Bremia, Peronospora, Plasmopara, Pseudoperonospora* and *Sclerospora* (causing downy mildews), *Erysiphe graminis* (causing powdery mildew of cereals and grasses), *Verticillium* (causing vascular wilts of vegetables, flowers, crop plants and trees), *Rhizoctonia* (causing damping off disease of many plants and brown patch disease of turfgrasses), *Fusarium* (causing root rot of bean, dry rot of potatoes), *Cochliobolus* (causing root and foot rot, and also blight of cereals and grasses), *Giberella* (causing seedling blight and foot or stalk rot of corn and small grains), *Gaeumannomyces* (causing the take-all and whiteheads disease of cereals), *Schlerotinia* (causing crown rots and blights of flowers and vegetables and dollar spot disease of turfgrasses), *Puccinia* (causing the stem rust of wheat and other small grains), *Ustilago* (causing corn smut), *Magnaporthae* (causing summer patch of turfgrasses), and *Schlerotium* (causing southern blight of turfgrasses). Other important fungal diseases include those caused by *Cercospora, Septoria, Mycosphoerella, Glomerella, Colletotrichum, Helminthosporium, Alterneria, Botrytis, Cladosporium* and *Aspergillus*.

Applicants also believe that PAP II proteins confer increased resistance to other plant pests including insects, bacteria and nematodes. Important bacterial diseases to which PAP II imparts increased resistance include those caused by *Pseudomonas, Xanthomonas, Erwinia, Clavibacter* and *Streptomyces*.

DNAs encoding PAP II proteins may be synthesized in accordance with standard techniques. See Ausubel et al. (eds.), Vol. 1, Chap. 8 in *Current Protocols in Molecular Biology*, Wiley, NY (1990). The DNAs may also be prepared via PCR techniques. See *PCR Protocols*, Innis, et al. (eds.), Academic Press, San Diego, Calif. (1990). The PAP II DNA (e.g., a cDNA) is preferably inserted into a plant transformation vector in the form of an expression cassette containing all of the necessary elements for transformation of plant cells. The expression cassette typically contains, in proper reading frame, a promoter functional in plant cells, a 5' non-translated leader sequence, the mutant PAP DNA, and a 3' non-translated region functional in plants to cause the addition of polyadenylated nucleotides to the 3' end of the RNA sequence. Promoters functional in plant cells may be obtained from a variety of sources such as plants or plant DNA viruses. The selection of a promoter used in expression cassettes will determine the spatial and temporal expression pattern of the construction in the transgenic plant. Selected promoters may have constitutive activity and these include the CaMV 35S promoter, the actin promoter (McElroy, et al. Plant Cell 2:163-171 (1990); McElroy, et al. Mol. Gen. Genet. 231:150–160 (1991); Chibbar, et al. Plant Cell Rep. 12:506–509 (1993), and the ubiquitin promoter (Binet, et al. Plant Science 79:87–94 (1991), Christensen, et al. Plant Mol. Biol. 12:619–632 (1989); Taylor, et al. Plant Cell Rep. 12:491–495 (1993)). Alternatively, they may be wound-induced (Xu, et al., Plant Mol. Biol. 22:573–588 (1993), Logemann, et al., Plant Cell 1:151–158 (1989), Rohrmeier, et al., Plant Mol. Biol. 22:783–792 (1993), Firek, et al. Plant Mol. Biol. 22:129–142 (1993), Warener, et al. Plant J. 3:191–201 (1993)) and thus drive the expression of the mutant PAP gene at the sites of wounding or pathogen infection. Other useful promoters are expressed in specific cell types (such as leaf epidermal cells, meosphyll cells, root cortex cells) or in specific tissues or organs (roots, leaves or flowers, for example). Patent publication WO 93/07278, for example, describes the isolation of the maize trpA gene which is preferentially expressed in pith cells. Hudspeth, et al., Plant Mol. Biol. 12:579–589 (1989), describes a promoter derived from the maize gene encoding phosphoenolpyruvate carboxylase (PEPC) with directs expression in a leaf-specific manner. Alternatively, the selected promoter may drive expression of the gene under a light-induced or other temporally-regulated promoter. A further alternative is that the selected promoter be chemically regulated.

A variety of transcriptional cleavage and polyadenylation sites are available for use in expression cassettes. These are responsible for correct processing (formation) of the 3' end of mRNAs. Appropriate transcriptional cleavage and polyadenylation sites which are known to function in plants include the CaMV 35S cleavage and polyadenylation sites, the tml cleavage and polyadenylations sites, the nopaline synthase cleavage and polyadenylation sites, the pea rbcS E9 cleavage and polyadenylation sites. These can be used in both monocotyledons and dicotyledons.

Numerous sequences have been found to enhance gene expression from within the transcriptional unit and these sequences can be used in conjunction with the genes of this invention to increase their expression in transgenic plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis, et al., Genes Develop 1:1183–1200 (1987)). In the same experimental system, the intron from the maize bronze-1 gene had a similar effect in enhancing expression (Callis, et al., supra.). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic mottle Virus (MCMV), and Alfalfa Mosaic Virus (AMV) have been shown to be effective in enhancing expression (e.g. Gallie, et al. Nucl. Acids Res. 15:8693–8711 (1987); Skuzeski, et al. Plant Mol. Biol. 15:65–79 (1990)).

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformations include the nptII gene which confers resistance to kanamycin (Messing, et al., Gene 19:259–268 (1982); Bevan, et al., Nature 304:184–187 (1983)), the bar gene which confers resistance to the herbicide phosphinothricin (White, et al., Nucl. Acids Res. 18, 1062 (1990); Spencer, et al., Theor. Appl. Genet. 79:625–631 (1990)), the hph gene which confers resistance to the antibiotic hygromycin (Blochinger, et al., Mol. Cell Biol. 4:2929–2931)), and the dhfr gene, which confers resistance to methotrexate. Vectors suitable for *Agrobacterium* transformation typically carry at least one T-DNA border sequence. These include vectors such as pBIN19 and pCIB200 (EP 0 332 104).

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on *Agrobacterium* include transformation via particle bombardment, protoplast uptake (e.g. PEG and electroporation) and microinjection. The choice of vector depends largely on the preferred selection for the species being transformed. For example, pCIB3064 is a pUC-derived vector suitable for the direct gene transfer technique in combination with selection by the herbicide basta (or phosphinothricin). It is described in WO 93/07278 and Koziel, et al., Biotechnology 11:194–200 (1993).

An expression cassette containing the mutant PAP gene DNA containing the various elements described above may be inserted into a plant transformation vector by standard recombinant DNA methods. Alternatively, some or all of the elements of the expression cassette may be present in the vector, and any remaining elements may be added to the vector as necessary.

Transformation techniques for dicotyledons are well known in the art and include *Agrobacterium*-based techniques and techniques which do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery or microinjection. Examples of these techniques are described by Paszkowski, et al., EMBO J. 3:2717–2722 (1984), Potrykis, et al., Mol. Gen. Genet. 199:169–177 (1985), Reich, et al., Biotechnology 4:1001–1004 (1986), and Klein, et al., Nature 327:70–73 (1987). In each case the transformed cells are regenerated to whole plants using standard techniques.

*Agrobacterium*-mediated transformation is a preferred technique for transformation of dicotyledons because of its high efficiency of transformation and its broad utility with many different species. The many crop species which are routinely transformable by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (*Brassica*), U.S. Pat. No. 4,795,855 (poplar)). *Agrobacterium* transformation typically involves the transfer of the binary vector carrying the foreign DNA of interest (e.g. pCIB200 or pCIB2001) to an appropriate *Agrobacterium* strain which may depend on the complement of vir genes carried by the host *Agrobacterium* strain either on a co-resident plasmid or chromosomally (e.g. strain CIB542 for pCIB200 (Uknes, et al., Plant Cell 5:159–169 (1993)). The transfer of the recombinant binary vector, to *Agrobacterium* is accomplished by a triparental mating procedure using *E. coli* carrying the recombinant binary vector, a helper *E. coli* strain which carries a plasmid such as pRK2013 which is able to mobilize the recombinant binary vector to the target *Agrobacterium* strain. Alternatively, the recombinant binary vector can be transferred to *Agrobacterium* by DNA transformation (Höfgen, et al., Nucl. Acids Res. 16, 9877 (1988)).

Transformation of the target plant species by recombinant *Agrobacterium* usually involves co-cultivation of the *Agrobacterium* with explants from the plant and follows protocols known in the art. Transformed tissue is regenerated on selectable medium carrying an antibiotic or herbicide resistance marker present between the binary plasmid T-DNA borders.

Preferred transformation techniques for monocots include direct gene transfer into protoplasts using PEG or electroporation techniques and particle bombardment into callus tissue. Transformation can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher, et al., Biotechnology 4:1093–1096 (1986)).

Published European and International Patent Applications EP O 292 435, EP O 392 225 and WO 93/07278 describe techniques for the preparation of callus and protoplasts of maize, transformation of protoplasts using PEG or electroporation, and the regeneration of maize plants from transformed protoplasts. Gordeon-Kamm, et al., Plant Cell 2:603–618 (1990), and Fromm, et al., Biotechnology 11:194–200 (1993), describe techniques for the transformation of elite inbred lines of maize by particle bombardment.

Transformation of rice can also be undertaken by direct gene transfer techniques utilizing protoplasts or particle bombardment. Protoplast-mediated transformation has been described for *Japonica*-types and *Indica*-types (Zhange, et al., Plant Cell Rep. 7:739–384 (1988); Shimamoto, et al. Nature 338:274–277 (1989); Datta, et al. Biotechnology 8:736–740 (1990)). Both types are also routinely transformable using particle bombardment (Christou, et al. Biotechnology 9:957–962 (1991)).

European Patent Application EP 0 332 581 described techniques for the generation, transformation and regeneration of Pooideae protoplasts. Furthermore wheat transformation has been described in Vasil, et al. (Biotechnology 10:667–674 (1992)) using particle bombardment into cells of type C long-term regenerable callus, and in Vasil, et al. (Biotechnology 11:1553–1558 (1993)) and Weeks, et al. (Plant Physiol. 102:1077–1084 (1993)) using particle bombardment of immature embryos and immature embryo-derived callus.

Transformation of monocot cells such as *Zea mays* can be achieved by bringing the monocot cells into contact with a multiplicity of needle-like bodies on which these cells may be impaled, causing a rupture in the cell wall thereby allowing entry of transforming DNA into the cells. See U.S. Pat. No. 5,302,523. Transformation techniques applicable to both monocots and dicots are also disclosed in the following U.S. patents: U.S. Pat. No. 5,240,855 (particle gun); U.S. Pat. No. 5,204,253 (cold gas shock accelerated microprojectiles); U.S. Pat. No. 5,179,022 (biolistic apparatus); U.S. Pat. Nos. 4,743,548 and 5,114,854 (microinjection); and U.S. Pat. Nos. 5,149,655 5,120,657 (accelerated particle mediated transformation); U.S. Pat. No. 5,066,587 (gas driven microprojectile accelerator); U.S. Pat. No. 5,015,580 (particle-mediated transformation of soy bean plants); U.S. Pat. No. 5,013,660 (laser beam-mediated transformation); and U.S. Pat. Nos. 4,849,355 and 4,663,292.

The thus-transformed plant cells or plant tissue are then grown into full plants in accordance with standard techniques. Transgenic seed can be obtained from transgenic flowering plants in accordance with standard techniques. Likewise, non-flowering plants such as potato and sugar beets can be propagated by a variety of known procedures. See, e.g. Newell, et al. Plant Cell Rep. 10:30–34 (1991) (disclosing potato transformation by stem culture).

PAP II proteins confer broad spectrum fungus and/or virus resistance to a wide variety of plant types, including monocots (e.g., cereal crops) and dicots. Specific examples include maize, tomato, turfgrass, asparagus, papaya, sunflower, rye, beans, ginger, lotus, bamboo, potato, rice, peanut, barley, malt, wheat, alfalfa, soybean, oat, eggplant, squash, onion, broccoli, sugarcane, sugar beet, beets, apples, oranges, grapefruit, pear, plum, peach, pineapple, grape, rose, carnation, daisy, tulip, Douglas fir, cedar, white pine, scotch pine, spruce, peas, cotton, flax and coffee. As an alternative to preparing transgenic plants containing an exogenous PAP II gene (or a PAP II transgene), PAP II may be applied directly onto the plants.

Other PAP II proteins that exhibit substantially no cytotoxicity e.g., phytotoxicity can be identified using a selection system in eukaryotic cells as disclosed in U.S. Pat. Nos. 5,756,322 and 5,880,329 in connection with PAP. In a preferred embodiment, a PAP II DNA molecule, operably linked to an inducible promoter functional in the eukaryotic cell, is randomly mutagenized in accordance with standard techniques. The cell is then transformed with the mutagenized PAP II construct. The thus-transformed cell is then cultured in a suitable medium for a predetermined amount of time, e.g., sufficient to cause some growth of the cells, at which time an inducer is added to the medium to cause expression of the mutagenized DNA molecule. Then an observation is made as to whether the cultured cell survives the induction of the expression of the mutagenized PAP II DNA. Survival indicates that the mutagenesis resulted in the expression of a non-toxic PAP II mutant. The PAP II mutant then can be tested in vitro or in vivo to determine whether it exhibits PAP II anti-viral and/or anti-fungal activity. Preferred in vitro assays include eukaryotic translation systems such as reticulocyte lysate systems wherein the extent of the inhibition of protein synthesis in the system caused by the PAP II mutant is determined. Preferred host cells are yeast cells such as *Saccharomyces cerevisiae*. This method can also be conducted with a plurality of randomly mutagenized PAP II DNAs. The PAP II mutants identified as non-toxic and possessing PAP II anti-viral and/or anti-fungal activity, as determined by subsequent assays, can then be isolated, purified and sequenced in accordance with standard techniques.

In another embodiment, the mutagenesis is performed after the transformation of the eukaryotic cell. The disadvantage with mutagenizing the PAP II DNA after transformation is that the chromosomal DNA of the host can also be mutagenized. To determine whether the mutations of the surviving cells are chromosomal or plasmid-borne in nature, this embodiment requires the step of replacing the transforming PAP II DNA with wild-type PAP II DNA under the control of an inducible promoter, and growing the cells in the presence of the inducer. Mutants which retain the ability to grow are chromosomal mutants, whereas mutants which fail to grow are plasmid-borne (i.e., PAP II) mutants.

The invention will be further described by reference to the detailed examples. These examples are provided for purposes of illustration only, and are not intended to be limiting unless otherwise specified.

EXAMPLES

Example 1

Cloning of PAP II Gene and Comparative Toxicities of PAP I and PAP II in Transformed Tobacco PAP was purchased from Calbiochem, PAP II was a generous gift of Dr. James Irvin. Polyclonal antibodies against PAP and PAP II were raised in rabbits. PAP II IgG was purified using a protein A affinity column (Bio-Rad, Hercules, Calif.). Alkaline-phosphatase (Sigma, St. Louis, Mo.) was conjugated to PAP II IgG by glutaraldehyde (Harlow, et al., "Immunoblotting". In: *Antibodies: A Laboratory Manual*, pp. 471–510, Cold Spring Harbor Laboratory, Cold Spring Harbor, N.Y. (1988)).

Cloning of PAP II cDNA

Total RNA was isolated from 1 gram of pokeweed leaves using Tri-Reagent (Molecular Research Center, Cincinnati, Ohio). Poly A+ RNA was isolated using an oligo-dT affinity resin (Stratagene, LaJolla, Calif.). The cDNA library was constructed from 5 µg total mRNA with a lambda ZAP-cDNA synthesis kit according to the manufacturer's instructions (Stratagene, LaJolla, Calif.). The cDNA library, the titer of which was $6.25 \times 10^8$ pfu/µg, was transferred to nitrocellulose and probed with $8 \times 10^6$ cpm of $^{32}$P-labeled oligonucleotide 5'GGGTTGTTCAGTGAGGGTTGTG-GCC3' (SEQ. ID NO:5) corresponding to the N-terminal region of PAPII cDNA (Poyet, et al., FEBS Lett 347: 268–272 (1994)). Four clones with approximately 1 kb inserts were sequenced using the dideoxy chain termination method.

Plant Transformation Vector and Tobacco Transformation

A full-length PAP II cDNA insert in pBluescript SK+/− was digested with PvuII at its 5' end and XhoI at its 3' end. The PvuII/XhoI fragment containing PAPII was cloned into the SmaI site of the plant transformation vector pMON977. The resulting plasmid contained the PAPII transgene under the control of the 35S promoter from cauliflower mosaic virus and selectable marker neomycin phosphotransferase (NPTII) under the control of the nopaline synthase promoter. The recombinant vector NT159 was introduced to tobacco (*Nicotiana tabacum* cv. Samsun (NN)) by *Agrobacterium*-mediated transformation. Transgenic plants generated were screened by ELISA for expression of NPTII and PAP II. The lines that showed expression of both NPTII and PAP II were self-pollinated and $R_1$ progeny obtained. Homozygous $R_2$ progeny were selected by germination of $R_1$ seeds on MS plates containing 100 µg/ml kanamycin.

Virus Resistance Tests $R_1$ progeny from transgenic lines (six leaf stage) were evaluated for resistance to tobacco mosaic virus (TMV, U1 strain) and potato virus X (PVX). Two leaves of each plant were mechanically inoculated with each virus in 50 mM potassium phosphate buffer (pH 7.5) in the presence of carborundum. The inoculated plants were placed in a growth chamber for symptom development (conditions: 14 hour day length, 60% humidity, temperature 23° C. during daytime and 19° C. at night). The lesion numbers on inoculated leaves were scored 4 days post inoculation for TMV and 10 days post inoculation for PVX. Four leaf discs from the inoculated leaves were sampled with a cork borer (size 7) and homogenized in 150 µl of cold phosphate-buffered saline (PBS, pH 7.5) containing protease inhibitors (1 µg/ml leupeptin, 1 µg/ml pepstatin A, 1 µg/ml antipain and 100 µg/ml PMSF). The homogenate was placed on ice for 10 min, centrifuged at 14,000 rpm in a microfuge for 5 minutes and the supernatant containing soluble proteins was used for either western blot or ELISA analysis.

Fungal Resistance Tests

Fungal cultures (*Rhizoctonia solani*) were incubated in the dark at 30° C. for 48 hours on potato dextrose agar plates. Pathogen cultures were homogenized and suspended in sterile water and mixed with sterile soil (5 plates for 3 liters of soil). Four-week old transgenic and control seedlings were transplanted into the inoculated soil. Transplanted seedlings were kept under plastic domes to maintain humidity. Development of disease symptoms was observed for eighteen days and the seedling mortality rate was calculated.

Western Blot Analysis

Total soluble protein (20 µg) was separated on a 12.5% acrylamide gel together with a PAP II standard (10 ng). The resolved proteins were transferred to a nitrocellulose membrane using a BioRad trans-blot apparatus. The membrane was blocked in 5% non-fat milk in PBS buffer containing 0.1% tween-20 (PBS-T) for one hour, and then incubated with PAP II antiserum (1:500 dilution) overnight at 4° C. Following washing with PBS-T, the membrane was incubated with horse-radish peroxidase conjugated goat anti-rabbit IgG (1:5000) at room temperature for 1 hour and developed with a "Renaissance" chemiluminescence detection kit (Dupont, Wilmington, Del.).

The membrane was stripped by incubation in 8M guanidine hydrochloride at room temperature for 30 min. The membrane was then washed four times (15 min each) with PBS-T buffer, blocked in PBS-T containing 5% non-fat milk for 30 min and probed with monoclonal antibodies against PR1 (1:1000).

ELISA Analysis

PVX antigen levels were determined by ELISA as described in Hur, et al., Proc. Natl. Acad. Sci. 92:8448–8452 (1995). An ELISA plate was coated with 1 µg of PAP II IgG per well, to conduct PAP II ELISA. Soluble protein plant extracts (100 µl) prepared as described for virus resistance analysis, were added to the plates and the plates were incubated overnight at 4° C. Bound PAPII was detected with alkaline phosphatase-conjugated anti-PAP II IgG (1:1000).

Salicylic Acid Analysis

Leaf tissue (0.3 g) was collected from young expanded leaves of 5-week old plants from each transgenic and control tobacco line, homogenized in liquid nitrogen and SA was extracted as described by Yalpani, et al., Phytopathology 83:702–708 (1993). Leaf tissue from four different transgenic and wild type plants was analyzed. Free and total SA were detected by high-performance liquid chromatography and SA levels were quantified. Yalpani, et al., supra.

Results

PAPII cDNA Cloning and Analysis

A cDNA library was constructed in the lambda ZAP vector using polyA+ RNA from *Phytolacca americana* leaves. The cDNA library was screened with a primer corresponding to the 5' terminal sequence of PAP II. Poyet, et al., FEBS letters 347:268–272 (1994). Four putative clones that hybridized to the oligonucleotide probe were sequenced. All four clones had the same 933 bp coding sequence and were identical to the previously described PAP II cDNA. See Poyet, et al., supra. Protein sequence predicted from the nucleotide sequence of the cDNA clone showed that PAP II has an extra 25 amino acids at its N-terminus that are not present in the mature protein (Bjorn, et al., Biochimica et Biophysica Acta. 790:154–63 (1984)). Comparison of the protein sequences of PAP II and PAP indicated that PAP II has only 41% identity to PAP and only 20% identity within the last 80 amino acids at the C-terminus. PAP II has no putative lipoprotein lipid attachment site at its C-terminus as previously described for PAP, Hur, et al., supra.

Expression and Toxicity of PAPII in Transgenic Tobacco

The full length PAP II cDNA was inserted into a plant transformation vector under the control of the cauliflower mosaic virus 35S promoter. The resulting vector, NT159 was introduced into *Nicotiana tabaccum* cv. Samsun NN by *Agrobacterium*-mediated transformation. *N. tabacum* transformation frequencies, defined as the number of transgenic plants obtained per initial leaf disk times 100, were only slightly reduced for NT159 (5%) compared to the vector control (7–10%). The transformation frequencies were significantly higher for NT159 containing PAP II (5%) compared to 33617, which contains the wild type PAP (0.7%). Lodge, et al., Proc. Natl. Acad. Sci. 90:7089–7093 (1993). Eight different independently transformed tobacco lines positive for NPTII and PAP II expression by ELISA were obtained. All eight $R_0$ lines produced viable seeds. PAP II protein expressed in transgenic tobacco had the same electrophoretic mobility as mature PAP II isolated from pokeweed, indicating that PAP II expressed in transgenic tobacco was processed in a similar fashion as in pokeweed (photograph not shown). The cross-reacting lower molecular weight polypeptide observed in the wild type plant (W.T.) was not consistently observed in other untransformed tobacco plants (photograph not shown).

Levels of PAP II expression in the eight independent transgenic lines varied. $R_1$ progeny plants from line 159-9 expressed high levels of PAP II protein (up to 250 ng/mg protein) by immunoblot analysis, while plants from $R_1$ progeny of line 159-8 had moderate levels of PAP II expression (20–100 ng/mg protein). A few plants from line 159-9 showed chlorotic lesions on their leaves, as previously observed in transgenic plants expressing PAP and PAP-variant Lodge, et al., supra. To determine if the presence of these lesions correlated with the levels of PAP II expression, plants from $R_1$ progeny of line 159-9 with or without chlorotic lesions were analyzed for expression of PAP II using immunoblot analysis. Individual plants that showed chlorotic lesions expressed higher levels of PAP II (above 150 ng/mg protein) than those that did not have lesions (less than 100 ng/mg protein) (photograph not shown). $R_1$ progeny from line 159-8 expressing 10–80 ng/mg PAP II appeared perfectly normal (photograph not shown). These results indicate that PAP II is expressed at least 10-fold higher levels than wild type PAP in transgenic tobacco plants (Lodge, et al., supra). The higher accumulation of PAP II in transgenic tobacco plants and the higher transformation frequencies observed with PAP II containing vectors indicate that PAP II is less toxic to transgenic plants than PAP.

Antiviral Activity of Transgenic Tobacco Expressing PAP II

To determine if transgenic tobacco plants expressing PAP II are resistant to viral infection, self-fertilized $R_1$ progeny from transgenic lines were screened for the presence of PAP II by ELISA, and only PAP II-positive plants were used in the virus resistance tests. $R_1$ progeny from line 159-9 (159-91), with high levels of PAP II and $R_1$ progeny from lines 159-8 (159-81 and 159-82), with lower levels were challenged with 0.1 μg/ml TMV and 5 μg/ml PVX. Symptom development on both inoculated and upper leaves was monitored visually each day up to 21 days post inoculation. Plants from line 159-91 with high levels of PAP II (150 ng of PAP II per mg of total protein by ELISA) were evaluated in the same experiment along with wild type tobacco plants. The results are shown in Table 3.

TABLE 3

Susceptibility of Transgenic Tobacco Plants Expressing PAP II to Infection by TMV and PVX

| Lines | PAP II§(ng/mg) | TMV# Number of HR Lesion | PVX¶ Number of Lesion |
|---|---|---|---|
| W.t | 0 | 90 ± 29 | 94 ± 6 |
| 159-91 | 150 ± 20 | 18 ± 20* | 10 ± 3* |
| W.t | 0 | 85 ± 34 | 93 ± 27 |
| 159-81 | 20 ± 5 | 30 ± 23* | 41 ± 31* |
| 159-82 | 11 ± 2 | 34 ± 24* | 52 ± 29* |

§Five wild type plants and ten plants from $R_1$ progeny of each tobacco line were analyzed by ELISA for expression of PAP II. Mean value ± SD are shown, and expressed as ng of PAP II per mg of total plant protein.
Ten transgenic plants (Samsun NN) were inoculated with TMV 0.1 μg/ml. After three days of postinoculation, the numbers of lesions were counted.
¶Ten plants (Sansun NN) were inoculated with PVX at 5 g/ml. After 12 days, the number of local lesions on the inoculated leaves were counted.
*Significantly different from wild type at 1% level.

As shown in Table 3 (upper panel), plants from line 159-91 showed 80% reduction in TMV lesion numbers compared to the control plants. Plants from lines 159-81 and 159-82, with lower levels of PAP II (20 and 11 ng PAP II per mg total protein by ELISA), evaluated in another experiment, showed 65% and 60% reduction in TMV lesion numbers, respectively compared to the control plants (Table 3, lower panel). Similar results were obtained when transgenic plants expressing PAP II were inoculated with potato virus X (PVX) (Table 3). Line 159-91 showed an 89% reduction in PVX lesion numbers 10 days post inoculation, while lines 159-81 and 159-82 showed 56% and 44% reduction in PVX lesion numbers, respectively. Similarly, a fewer percentage of PAP II expressing plants showed PVX lesions on their upper leaves compared to the control plants.

These results demonstrate that all transgenic lines tested had dramatically reduced numbers of TMV and PVX lesions and the level of resistance to viral infection correlated well with PAP II protein levels in transgenic plants.

Anti-Fungal Activity of Transgenic Tobacco Expressing PAP II

One month after germination, twenty seedlings from homozygous progeny ($R_2$ generation) of five different independently transformed lines were transplanted into soil inoculated with the pathogenic fungus *Rhizoctonia solani*. Plants were kept under plastic domes throughout the experiment to maintain high relative humidity. Disease progression was monitored for three weeks and the percentage of dead seedlings recorded at six, ten, fourteen, and eighteen days post transplanting. Seedling mortality and disease development are shown in FIG. 1. Two weeks post transplanting, 90% of the control seedlings were dead. All transgenic lines tested were less susceptible to disease. The most resistant lines were 159-91, 159-92 and 159-81. In these lines seedling mortality rate was much less (30% to 40%) compared to the control (90%).

In contrast to the most resistant lines, one transgenic line (159-82) showed a lower level of resistance. Six days after transplanting into fungus infested soil, 50% of control seedlings were dead, compared to only 35% in line 159-82. By two weeks post transplanting, 90% of the control seedlings were dead, compared to 75% in line 159-82. Examination of PAP II levels in the transgenic lines that survived fungal infection showed that PAP II was expressed in each plant (data not shown). Homozygous progeny from lines 159-91 and 159-92, which expressed the highest levels of PAP II, showed the highest levels of resistance. Homozygous progeny from line 159-81 that survived fungal infection, expressed PAP II at similar levels as plants from line 159-92. Homozygous progeny from line 159-82, which expressed the lowest levels of PAP II, showed the lowest level of resistance.

PR Expression in Transgenic Tobacco Plants Expressing PAP II

It was recently shown that pathogenesis-related proteins (PR-proteins) are induced in transgenic plants expressing PAP. Zoubenko, et al., Nature/Biotechnology 15:992-996 (1997). In many plants including tobacco, the primary infection can trigger an enhanced systemic resistance of the plant to subsequent infection by a variety of pathogens. This nonspecific resistance is known as systemic acquired resistance (SAR) and is associated with the systemic de novo synthesis of a large number of PR proteins. To determine if PR protein expression is induced in transgenic plants expressing PAP II, PAP II and PR1 expression were analyzed in $R_1$ progeny of five different transgenic lines by immunoblot analysis using polyclonal antibodies against PAP II and monoclonal antibodies against PR1. All five transgenic lines expressed PAP II and PR1 (photograph not shown). The level of PR1 expression in transgenic lines correlated well with the levels of PAP II protein (photograph not shown). Lines 159-91, 159-92 and 159-93, which expressed higher levels of PAP II, showed higher levels of PR1 (photograph not shown). Lines 159-81 and 159-82, which expressed lower levels of PAP II, showed lower amounts of PR1 accumulation (photograph not shown). PR1 levels in lines 159-81 and 159-82 were similar to the PR1 levels in wild type plants inoculated with TMV (photograph not shown).

Analysis of Salicylic Acid Levels in Transgenic Lines Expressing PAP II

PR-protein synthesis is induced in response to pathogen attack and correlates well with the induction of SAR that confers nonspecific resistance in the distal parts of plants against different kinds of pathogens. Activation of SAR in plants is closely linked with the induction of salicylic acid (SA) synthesis. To determine if SA levels are elevated in transgenic plants expressing PAP II, free and total SA levels were analyzed in different transgenic lines. As shown in FIG. 2, free SA levels in transgenic plants expressing PAP II were similar to the controls. Similar results were obtained when total SA levels were analyzed (data not shown).

PAP II accumulates in the leaves of pokeweed plants grown in the summer. Unlike PAP, PAP II expression in pokeweed is induced upon environmental stress (unpublished data). PAP II has very low sequence homology to PAP, suggesting that it may have a different physiological function. The physiological function of RIPs is not known. They are viewed as defense-related proteins because some RIPs such as PAP deadenylate ribosomes from all organisms, and their expression in transgenic plants leads to resistance to viral and fungal infection. See Gornhardt, et al., Plant J. 8:97–109 (1995), Lodge, et al., Proc. Natl. Acad. Sci. 90:7089–7093 (1993), Logemann, et al., Bio/Technology 10:305–308 (1992). Expression of several RIPs is induced by environmental stress. See Reinbothe, et al., Plant Cell 6:1197–1209 (1986), Rippmann, et al., Plant. Mol. Biol. 35:701–709 (1997), and Stirpe, et al., FEBS Lett. 382: 309–312 (1996). It has been suggested that these RIPs may regulate protein synthesis during stress. See Gorschen, et al., Planta 202:470–478 (1997) and Rippman, et al., supra.

PAP II contains a 25 amino acid signal sequence at its N-terminus and like PAP it may also be localized in the cell wall. See Ready, et al., Proc. Natl. Acad. Sci. 83:5053–5056 (1986). The results indicate that PAP II is significantly less toxic to transgenic tobacco than PAP in terms of the relative transformation frequencies, phenotype of transgenic plants and the level of transgene expression. Since PAP and PAP II have similar N-glycosylase activity in vitro, the differences in their cytotoxicity may not be due to differences in their enzymatic activity. Again, without intending to be bound by any particular theory of operation, the different cytotoxicities of PAP and PAP II may be due to their ability to enter the cytosol. It has been shown that ricin A chain is translocated from the endoplasmic reticulum to the cytosol via a retrograde transport pathway. Rapak, et al., Proc. Natl. Acad. Sci. U.S.A. 24:3783–3788 (1997). It has been previously shown that toxicity of PAP is not due solely to enzymatic activity, but involves specific residues at the N-terminal and C-terminal regions of the protein Hur, et al., Proc. Natl. Acad. Sci. 92:8448–8452 (1995). The C-terminal 25 amino acids of PAP appear to be critical for cytotoxicity because deletion of these sequences abolishes toxicity towards yeast and transgenic plants (Hur, et al., supra.) PAP and PAP II are only 20% homologous in this region. The low sequence homology at the C-terminal regions of PAP and PAP II suggests that the sequence differences near the C-terminus may account for the differences in their toxicity.

Two phenotypically normal transgenic tobacco lines expressing the PAPII gene were resistant to both viral and fungal infection. The mechanism of antiviral and antifungal activity of ribosome inactivating proteins from pokeweed remains to be elucidated. Based on current data, several models could be proposed. Again, without intending to be found by any particular theory of operation, they are as follows. In one model, PAP and PAP II, localized in the cell wall, enter the cell along with the pathogen and indirectly inhibit pathogen propagation by inactivating host ribosomes, thus killing infected cells. Ready, et al., supra. In support of this model, positive correlations were reported between depurination of host ribosomes and antiviral activity of exogenously applied RIPs in tobacco against TMV. Taylor, et al., Plant J. 5:827–835 (1994). Applicants have recently demonstrated, however, that a non-toxic C-terminal truncated PAP mutant which did not have detectable ribosome specific depurination activity in viva, had antiviral activity when expressed in transgenic tobacco, suggesting that antiviral activity of PAP can be dissociated from its toxicity. Tumer, et al., Proc. Natl. Acad. Sci. 94:3866–3871 (1997). PAP and other RIPs have been shown to depurinate RNA and DNA substrates in addition to rRNA. Barbieri, et al., Nucleic Acids Research 25:518–522 (1997). Thus, PAP and PAP II may directly attack a pathogen by affecting viral nucleic acid or by depurinating fungal ribosomes.

Another model or hypothesis is that PAP or PAP II expression activates host defense pathways and lead to broad spectrum resistance to pathogen infection, similar to SAR, which is characterized by activation of a signal transduction pathway and synthesis of a number of defense gene products. Applicants have previously shown that the expression of PR proteins is induced in transgenic plants expressing PAP and nontoxic PAP mutants. Zoubenko, et al., Nature/Biotechnology 15:992–996 (1997). These include chitinases and β-1,3-glucanases with proven lytic activity against fungal cell walls. Thus, it is possible that PAP and PAP II access ribosomes of the pathogen by penetrating the cells of invading hyphae by dual action of the transgenes and the host genes that are induced in transgenic plants.

The results demonstrate that transgenic tobacco plants expressing PAP II constitutively express the pathogenesis-related protein PR1 in the absence of pathogen infection or hypersensitive response. The level of PR1 produced correlates well with the level of PAP II expression, indicating that defense mechanisms are activated in transgenic plants expressing PAP II. Previously, Applicants argued that pathogen resistance in transgenic plants expressing PAP is not due to classical SAR. The apparent activation of defense responses employs a signal transduction pathway different from that involving salicylic acid. Zoubenko et al., supra. This theory is supported further by grafting experiments, in which we showed that transgenic tobacco rootstocks expressing PAP induce resistance to virus infection in both wild type *N. tabacum* NN and nn scions in the absence of elevated SA levels. Smirnov, et al., Plant Physiology 114: 1113–1121 (1997). These results suggested that PAP expression generates a signal that can translocate across the graft union and induce nonspecific resistance in wild type plants. Smirnov, et al., supra. It appears that PAP II transgenic plants exhibit the same type of pathogen resistance as was reported for PAP transgenic plants.

The results demonstrate that although PR1 is constitutively expressed, SA levels are not elevated in PAP II expressing transgenic plants. This is in sharp contrast with the five to tenfold increase necessary for efficient expression of PR proteins. Yalpani, et al., Phytopathology 83:702–708 (1993). These results suggest that both proteins activate a signal transduction pathway different from that controlling SAR or a downstream regulatory signal. Jordanov, et al., Mol. Cell. Biol. 17:3373–3381 (1997), reports that in mammalian cells, inactivation of translationally active ribosomes by ribotoxic agents, including the ribosome inactivating proteins a-sarcin and ricin A chain, strongly induced the stress-activated signal transduction pathway. In the case of PAP, both pathogen and stress-inducible host genes were activated even in transgenic lines expressing nontoxic PAP mutants. Zoubenko, et al., supra. In PAP II transgenic plants, PR1 expression was observed in lines that express low levels of PAP II that are phenotypically normal, suggesting that PR protein expression is not induced due to severe perturbation of plant metabolism. However, the resistance observed in PAP and PAP II transgenic lines, in the absence of visible signs of stress, may not exclude a possible involvement of at least some components of the stress-activated signal transduction pathway.

Example 2

Expression of Various PAP II Mutants in Yeast

Construct for Expression of PAP II in *Saccharomyces cerevisiae*

Plasmid containing the wild PAP II (NT148) was digested with PvuII and XhoI. Following electrophoresis in low melting agarose gel, the restriction fragments containing the PAP II inserts were purified and ligated to the yeast expression vector TKB175 digested with SmaI and XhoI. The resulting plasmid NT264, contained the selectible marker TRP and PAP II downstream of the galactose-inducible promoter, GAL1.

Site-Directed Mutagenesis of PAP II cDNA.

Point mutations were introduced into PAP II by site-directed mutagenesis using a Quick-Change™ Mutagenesis Kit (Stratagene) following the manufacturer's instructions. In each mutagenesis experiment, two complementary primers containing a desired point mutation were designed. The PCR mixture contained 125 ng of each primer, 100 ng plasmid DNA template containing PAP II cDNA(NT264), 0.5 mM dNTP and 3 units of Pfu DNA polymerase. PCR was run for 16 cycles (95° C. for 30 sec. 55° C. for 1 min and 68° C. for 12 min; for two nucleotide mutations, time was extended to 18 min). At the end of PCR, 1 unit of DpnI restriction enzyme was added to the PCR products for digestion of the parental methylated plasmid DNA at 37° C. for 1 hr. Five mircoliters of the DpnI digested PCR products were used for transformation of Epicurian Coli XL1-Blue Super-Competent cells (Stratagene) and plated on Amp+ LB. Mutagenized plasmids were isolated and the presence of the mutated nucleotide was confirmed by sequencing both strands of PAPII using the Sequenase 2.0 DNA Sequencing Kit (United States Biochemical). The primers for mutagenesis were as follows (wherein the numbering of amino acid as designed according to the mature sequence of PAP II):

NT288 (G72D)
G72DF: TTTGGAGGACTATTCTGAC (SEQ. ID NO:6)
G72DR: GTCAGAATAG TCCTCCAAA (SEQ. ID NO:7)
NT268 (E172V):
E173F: CCGTTCAAATGGTTACTGTGGCATCAAG-GTTC (SEQ. ID NO:8)
E173R: GAACCTTGATGCCACAGTAAC-CATTTGAACGG (SEQ. ID NO:9)
NT266(W238stop):
W238F: AAACCTTAGACTACGGCCAC (SEQ. ID NO:10)
W238R: GTGGCCGTAGTCTAAGGTTT (SEQ. ID NO:11)
NT288(W238R)
W238RF: AAACCTAGGACTACGGCCAC (SEQ. ID NO:12)
W238RR: GTGGCCGTAG TCCTAGGTTT (SEQ. ID NO:13)
NT309(L253A)
L253AF: CGACATTATGGCAGCCCTAACCCACGTTAC (SEQ. ID NO:14)
L253AR: GTAACGTGGG TTAGGGCTGC CATAAT-GTCG (SEQ. ID NO:15)
NT280 (L254R)
L254RF: CGACATTATGGCACTCCGAACCCACGT-TACTTGC (SEQ. ID NO:16)
L254RR: GCAAGTAACGTGGGTTCGGAGTGCCAT-AATGTCG (SEQ. ID NO:17)
NT271 (K260stop):
K260F: CACGTTACTTGCTAGGTTAAAAGTTC-CATGTTCC (SEQ. ID NO:18)
K260R: GGAACATGGAACTTTTAACCTAGCAAG-TAACGT (SEQ. ID NO:19)

Toxicity Assay of PAP II and its Mutants

Five micrograms of plasmid DNA containing wild type PAP II or PAP II mutants were transformed into yeast strain PSY1. One half of the transformation mix was plated onto the TRP-medium containing 2% raffinose and other half onto TRP-medium containing 2% galactose. Growth of the transformed yeast on the plates was monitored, and the number of transformants was recorded.

Analysis of PAP II Expression in Yeast

A single colony from the yeast transformation plate was first inoculated into 5 ml of liquid TRP-medium containing 2% raffinose and grown to a density $2 \times 10^6$ cells per ml. After harvesting, the cells were washed with water, and re-suspended in 20 ml TRP-medium containing either 2% raffinose or 2% galactose. Yeast cells were pelleted by centrifugation at 3000 rpm for 5 min in a table-top centrifuge. The tubes containing pellets were placed on ice for 5 min and an equal volume of 2× protein sample buffer containing the protease inhibitor mix (2 μg/ml Aprotinin, 2 μg/ml Leupeptin, 2 μg/ml Antipain, and 100 μg/ml PMSF, Sambrook, et al, *Molecular Cloning, A Laboratory Manual* (1989) and 50 μl acid-washed glass beads were added. The cells were lysed by vortexing the samples twice each for 2 min and kept on ice for 1 min. The lysates were boiled for 3 min and centrifuged for 5 min. Aliquots of samples were analyzed by immunoblot using PAP II antiserum.

Toxicity of Wild Type PAP II Expressed in Yeast

The results indicate that PAP II is significantly less toxic than PAP to transgenic tobacco plants. To determine if PAP II is as toxic to yeast as PAP, a full length PAP II cDNA was placed under a galactose-inducible GAL1 promoter and a PGK1 polyadenylation sequence at the 3' end of a yeast expression vector. The wild type PAP gene was introduced into the same vector as a control (NT209). The recombinant vectors NT264 (PAPII) or NT209 (PAP) with Trp– selection marker were introduced into *Saccharomyces cerevisiae*. All transformants harboring NT264 or NT209 were able to grow on the Trp– plate containing 2% raffinose but not on the Trp– plate containing 2% galactose. Comparison of the growth curves for yeast expressing PAP or PAP II showed that the pattern of growth inhibition by PAP II is similar to that observed with PAP, indicating that PAP II is as toxic as PAP when expressed in yeast. Immunoblot analysis showed that PAP II protein was expressed upon induction with galactose. The size of PAP II expressed in yeast is the same as purified PAP II from pokeweed leaves, indicating that PAP II is processed in yeast as it is in pokeweed.

Effect of Mutation of PAP II on its Toxicity to Yeast

Three-dimensional structures of many RIPs are similar but not identical. Sequence analysis of PAP II shows that active-site residues conserved in all RIPs are also conserved in PAP II. It has been shown that a mutation of PAP changing E176 to V at the active site region or changing W238 to a stop codon at the C-terminal region abolished the toxicity of PAP to yeast (Hur, et al., supra.). When the C-terminal deletion mutant of PAP was expressed in transgenic tobacco plants, the plants were phenotypically normal and were resistant to viral infection, suggesting that toxicity and antiviral activity could be dissociated.

To further dissect the toxicity mechanism and determine whether these residues important to toxicity of PAP are also important for toxicity of PAP II in yeast, nine mutations of PAP II were made by site-directed mutagenesis. The mutagenized PAP II genes were placed under a galactose-inducible GAL1 promoter in a yeast expression vector, and the toxicity of PAP II mutants was observed under both induced or uninduced conditions. The results are shown in Table 4.

TABLE 4

Effect of Mutations on Toxicity of PAPII to Yeast

| Constructs | Mutations | Toxicity |
|---|---|---|
| NT264 | Wild type | Yes |
| NT288 | G72D | None |
| NT268 | E172V | None |
| NT266 | W238stop | None |
| NT289 | W238R | Yes |
| NT309 | L253Astop | None |
| NT280 | L254R | None |
| NT307 | L254A | None |
| NT271 | K260stop | None |

The N-terminal region of PAP II contains a putative RNA binding region that is critical for recognition of RNA substrate. Two tyrosines plus two upstream arginine residues are conserved in most RIPs. Mutation of Glycine72 to charged aspartic acid abolished toxicity of PAP II to yeast (Table 4). It has been shown Y72 of PAP (Y69 in PAP II) interacts with adenine ring of the RNA substrate. G72D mutation may interrupt the interaction of Y72 with the RNA substrate and make it non-toxic to yeast.

E172 of PAP II is conserved among all RIPs and is a key residue at the active-site. In PAP, mutation of the equivalent residue (E176V) abolishes the toxicity and enzymatic activity of PAP. A similar mutation (E172V) was introduced to PAP II. The results show that E172V mutation abolished the toxicity of PAP II to yeast, indicating that this residue plays an important role in enzymatic activity (Table 4).

Previous studies showed that truncation of C-terminal 25 amino acid renders PAP nontoxic to yeast. Crystallographic data show that most of residues in this region are not directly involved in substrate binding or catalysis. One hypothesis is that this region might be involved in protein-membrane interaction, which is critical for PAP and PAP II to enter the cytosol. A series of single point mutations and truncations were made in the C-terminal region of PAP II. As in PAP, deletion of the C-terminal region after W238, a residue also conserved in PAP, resulted in a nontoxic phenotype. Without intending to be bound by any particular theory of operation, Applicants believe that the C-terminus of PAP and PAP II have similar functions.

Dileucine motif in many proteins has been shown to important in protein—protein interactions and in the protein sorting pathway. Applicants have discovered that PAP II and PAP also have a dileucine motifs at the C-terminal region, which might be important in sorting of PAP II and PAP. These sequences might be critical in interaction of PAP and PAP II with membranes. The dileucine residues are conserved in almost all RIPs, suggesting functional importance of these two residues. To investigate the function of the dileucine residues in PAP II, L253 was changed to alanine (NT309) and L254 was mutated to a short side chain residue alanine (NT307), or to a positive side chain residue arginine (NT280) or to a stop codon (NT309). The results in Table 4 show that all of these mutations abolished the cytotoxicity of PAP II to yeast, indicating that L253 and L254 are critical for toxicity to yeast and residues between L254 and stop codon are critical for toxicity of PAP II to yeast.

Example 3

Expression of PAP II in Turfgrass

An expression vector was constructed for turfgrass transformation which included the PAP II cDNA downstream of the maize ubiquitin promoter and intron in the plant expression vector NT168. Downstream of the PAP II gene, polyadenylation sequences from the small subunit of ribulose 1,5 bisphosphate carboxylase E9 gene were present. Transgenic turfgrass plants were generated using particle bombardment. Southern blot analysis identified several independently transformed lines containing PAP II sequences. Immunoblot analysis indicated very high levels of expression of PAP II protein in transgenic plants. The levels of expression of PAP II were greater than the levels observed with nontoxic PAP mutants. Transgenic plants were indistinguishable from wild type plants in their physical characteristics and appearance, indicating that PAP II expression was not toxic to turfgrass.

PAP II confers broad spectrum resistance to numerous pests. This resistance is provided efficiently in that a minimum number of transgenes is required. PAP II is also substantially non-phytotoxic and non-cytotoxic, and thus provides a distinct and unexpected advantage over the use of wild-type PAP. Transgenic plants that express PAP II gene are substantially more resistant to a variety of pathogens, including viruses, fungi, bacteria, nematodes and insects than comparable plants that do not express PAP II. Thus, higher crop yields will be obtained.

All publications mentioned in this specification are indicative of the level of skill of persons skilled in the art to which this invention pertains. All these publications are herein incorporated by reference to the same extent as if each individual publication was specifically and individually indicated to be incorporated by reference.

Various modifications of the invention described herein will become apparent to those skilled in the art. Such modifications are intended to fall within the scope of the appending claims.

INDUSTRIAL APPLICABILITY

The present invention is useful in the genetic engineering of plants, particularly crop plants that are susceptible to infestation by viruses and fungi. Imparting greater resistance to pests will increase crop yield.

The invention claimed is:

1. A transformed plant cell or part thereof containing a DNA molecule comprising a sequence encoding immature wild-type PAP II designated as SEQ ID NO:4, or wild-type mature PAP II designated as SEQ ID NO:21, or a mutant of SEQ ID NO:4 or 21 having a sequence containing E172 but that differs from SEQ ID NO:4 or 21 in terms of one amino acid substitution, a C-terminal deletion of up to 48 amino acid residues, or a combination of said substitution and said deletion, and wherein said mutant exhibits anti-viral and/or anti-fungal activity.

2. The transformed plant cell of claim 1 wherein said plant cell part is a protoplast.

3. The transformed plant cell of claim 1, wherein said DNA molecule comprises a sequence that encodes SEQ ID NO:4.

4. The transformed plant cell of claim 3, wherein said DNA molecule comprises SEQ ID NO:3.

5. The transformed plant cell of claim 1, wherein said DNA molecule comprises a sequence that encodes PAP II (1-285, G72D).

6. The transformed plant cell of claim 1, wherein said DNA molecule comprises a sequence that encodes PAP II (1-285, L254R).

7. The transformed plant cell of claim 1, wherein said DNA molecule comprises a sequence that encodes PAP II (1-285, L254A).

8. The transformed plant cell of claim 1, wherein said DNA molecule comprises a sequence that encodes PAP II (1-237).

9. The transformed plant cell of claim 1, wherein said DNA molecule comprises a sequence that encodes PAP II (1-259).

10. The transformed plant cell of claim 1, wherein said DNA molecule comprises a sequence that encodes a mutant of PAP II selected from the group consisting of PAP II (1-237), PAP II (1-238), PAP II (1-239), PAP II (1-240), PAP II (1-241), PAP II (1-242), PAP II (1-243), PAP II (1-244), PAP II (1-245), PAP II (1-246), PAP II (1-247), PAP II (1-248), PAP II (1-249), PAP II (1-250), PAP II (1-251), PAP II (1-252), PAP II (1-253), PAP II (1-254), PAP II (1-255), PAP II (1-256), PAP II (1-257), PAP II (1-258) and PAP II (1-259).

11. The transformed plant cell of claim 1, wherein said DNA molecule comprises a sequence that encodes PAP II (1-253, L253A).

12. The transformed plant cell of claim 1, wherein said DNA molecule comprises a sequence that encodes SEQ ID NO:21.

13. The transformed plant cell of claim 12, wherein said DNA molecule comprises SEQ ID NO:20.

14. A transgenic plant produced from the protoplast of claim 2.

15. The transgenic plant of claim 14, which is a monocot plant.

16. The transgenic plant of claim 15, wherein said monocot plant is a cereal crop plant.

17. The transgenic plant of claim 14, which is a dicot plant.

18. Transgenic seed from the transgenic plant of claim 14.

19. A DNA molecule comprising a sequence encoding a mutant immature wild-type PAP II designated as SEQ ID NO:4, or a mutant of wild-type mature PAP II designated as SEQ ID NO:21, or a mutant thereof having a sequence containing E172 but that differs from SEQ ID NO:4 or SEQ ID NO:21 in terms of one amino acid substitution, a C-terminal deletion of up to 48 amino acid residues, or a combination of said substitution and said deletion, and wherein said analog exhibits anti-viral and/or anti-fungal activity when expressed in plants.

20. The DNA molecule of claim 19, comprising a sequence that encodes a mutant of SEQ ID NO:4.

21. The DNA molecule of claim 20, comprising a sequence that encodes a mutant of SEQ ID NO:21.

22. The DNA molecule of claim 19, comprising a sequence that encodes PAP II (1-285, G72D).

23. The DNA molecule of claim 19, comprising a sequence that encodes PAP II (1-285, L254R).

24. The DNA molecule of claim 19, comprising a sequence that encodes PAP II (1-285, L254A).

25. The DNA molecule of claim 19, comprising a sequence that encodes PAP II (1-237).

26. The DNA molecule of claim 19, comprising a sequence that encodes PAP II (1-259).

27. The DNA molecule of claim 19, comprising a sequence that encodes a mutant of PAP II selected from the group consisting of PAP II (1-237), PAP II (1-238), PAP II (1-239), PAP II (1-240), PAP II (1-241), PAP II (1-242), PAP II (1-243), PAP II (1-244), PAP II (1-245), PAP II (1-246), PAP II (1-247), PAP II (1-248), PAP II (1-249), PAP II (1-250), PAP II (1-251), PAP II (1-252), PAP II (1-253), PAP II (1-254), PAP II (1-255), PAP II (1-256), PAP II (1-257), PAP II (1-258) and PAP II (1-259).

28. The DNA molecule of claim 19, comprising a sequence that encodes PAP II (1-253, L253A).

29. A recombinant vector comprising the DNA molecule of claim 19.

* * * * *

UNITED STATES PATENT AND TRADEMARK OFFICE
CERTIFICATE OF CORRECTION

PATENT NO. : 7,019,126 B1 Page 1 of 1
APPLICATION NO. : 09/721047
DATED : March 28, 2006
INVENTOR(S) : Nilgun E. Tumer and Pinger Wang It is certified that error appears in the above-identified patent and that said Letters Patent is hereby corrected as shown below:

TITLE Page, ITEM [75], "Turner" should read --Tumer--

Signed and Sealed this

First Day of August, 2006

JON W. DUDAS
*Director of the United States Patent and Trademark Office*